US012648992B2

(12) United States Patent
Kjaer et al.

(10) Patent No.: US 12,648,992 B2
(45) Date of Patent: Jun. 9, 2026

(54) CONDITIONS IMPROVING POXVIRUS STABILITY

(71) Applicant: Bavarian Nordic A/S, Hellerup (DK)

(72) Inventors: Katrine Kjaer, Brønshøj (DK);
Markus Kalla, Penzberg (DE)

(73) Assignee: Bavarian Nordic A/S, Hellerup (DK)

( * ) Notice: Subject to any disclaimer, the term of this patent is extended or adjusted under 35 U.S.C. 154(b) by 817 days.

(21) Appl. No.: 17/909,777

(22) PCT Filed: Mar. 12, 2021

(86) PCT No.: PCT/EP2021/056370
§ 371 (c)(1),
(2) Date: Sep. 7, 2022

(87) PCT Pub. No.: WO2021/180943
PCT Pub. Date: Sep. 16, 2021

(65) Prior Publication Data
US 2023/0114464 A1 Apr. 13, 2023

(30) Foreign Application Priority Data

Mar. 12, 2020 (EP) .................................... 20162856

(51) Int. Cl.
| | |
|---|---|
| *C12N 7/00* | (2006.01) |
| *A61K 39/285* | (2006.01) |
| *A61K 47/18* | (2017.01) |
| *A61K 47/26* | (2006.01) |
| *A61K 47/42* | (2017.01) |

(52) U.S. Cl.
CPC .......... *A61K 39/285* (2013.01); *A61K 47/183* (2013.01); *A61K 47/26* (2013.01); *A61K 47/42* (2013.01); *C12N 7/00* (2013.01); *C12N 2710/24034* (2013.01)

(58) Field of Classification Search
None
See application file for complete search history.

(56) References Cited

U.S. PATENT DOCUMENTS

2004/0265987 A1  12/2004  Trager et al.
2006/0110406 A1   5/2006  Kemble et al.

FOREIGN PATENT DOCUMENTS

| WO | 9912568 A1 | 3/1999 |
|---|---|---|
| WO | 2010036774 A1 | 4/2010 |
| WO | 2016087457 A1 | 6/2016 |
| WO | WO 2018211419 A1 | 11/2018 |

OTHER PUBLICATIONS

Cardoso et al., "Viral vaccine stabilizers: status and trends," Acta virologica, 2017, pp. 231-239, vol. 61.
White et al., "Development of a stable liquid formulation of live attenuated influenza vaccine," Vaccine, 2016, pp. 3676-3683, vol. 34.

*Primary Examiner* — M Franco G Salvoza

(57) ABSTRACT

The present invention relates to aqueous compositions conferring improved stability to poxvirus during storage as well as to the use of such compositions and methods for preparing the same. The compositions comprise recombinant human serum albumin (rHSA), gelatin or arginine, or combinations thereof.

21 Claims, 6 Drawing Sheets

CONDITIONS IMPROVING POXVIRUS STABILITY

FIELD OF THE INVENTION

The present invention relates to compositions conferring improved stability to poxvirus during storage. Particularly, the invention relates to aqueous compositions comprising recombinant human serum albumin (rHSA), gelatin or arginine, or combinations thereof. More particularly, the invention relates to such compositions comprising a poxvirus. The invention further relates to the use of such compositions and methods for preparing the same.

BACKGROUND OF THE INVENTION

Poxviruses including vaccinia virus and in particular modified vaccinia Ankara (MVA) virus have been developed as a vector for vaccines against infectious diseases such as HIV, influenza, malaria and respiratory syncytial virus (RSV) and for immunotherapies and oncolytic therapies against cancer (Choi and Chang *Clin Exp Vaccine Res* 2013, 2: 97-105; Rezaee et al. *Curr Opin Virol* 2017, 24: 70-78; Al Yaghchi et al. *Immunotherapy* 2015, 7: 1249-1258; Verheust et al. *Vaccine* 2012, 30: 2623-2632; Mastrangelo et al. *J Clin Invest* 2000, 105: 1031-1034). Several unique features make them ideal candidates for vaccine development or gene delivery: (i) large packaging capacity for recombinant DNA; (ii) precise recombinant DNA expression regulated by a strong poxviral promoter; (iii) lack of persistence or genomic integration in the host due to their cytoplasmic replication; (iv) high immunogenicity as vaccine; and (v) ease of vector and vaccine production (Verheust et al. *Vaccine* 2012, 30: 2623-2632).

Live, attenuated vaccines however form a formulation challenge because of its complex macromolecular structure of the virus. This is even more challenging with large enveloped viruses such as poxviruses. For examples, vaccinia virus such as MVA are very large (about 200-300 nm) enveloped double-stranded DNA viruses of about 192 kbps in size consisting of a core region composed of viral DNA and various enzymes encased in a lipoprotein core membrane. The outer layer consists of a double lipid membrane envelope (Al Yaghchi et al. *Immunotherapy* 2015, 7: 1249-1258). There are two major morphologically distinct infectious forms of virions, the intracellular mature virus (IMV) and extracellular enveloped virus (EEV). IMVs represent the majority of infectious particles which remain in the cytoplasm until lysis of the cells. EEVs are released from the cell and possess an extra lipid envelope with at least 10 associated proteins absent from IMV. The lipid membrane is very fragile and an important consideration since loss of the viral envelope results in viral inactivation. The stability can further vary considerably dependent on the preparations and excipients used for preparation of the purified viruses and its storage.

One difficulty is storage below the freezing point of water to avoid destabilization and/or disruption of the virus during freezing and thawing. In order to ensure stability, stocks of purified infective virus in the past were generally stored below minus 60 degrees centigrade. One problem of storing at such low temperatures is the potential to thaw and re-freeze during transit or at the site of administration.

The limited stability of live viruses in aqueous composition is well known, and most of the attenuated viruses are freeze-dried products such as for example the fully replication competent vaccinia virus ACAM2000. ACAM2000 was approved as a lyophilized preparation containing 6-8 mM HEPES (pH 6.5-7.5), 2% human serum albumin, 0.5-0.7% sodium chloride, 5% mannitol, and trace amounts of neomycin and polymyxin B. The lyophilized vaccinia virus was reconstituted in 50% (v/v) glycerol, 0.25% (v/v) Phenol in water for injection (Berhanu et al. *Vaccine* 2010, 29: 289-303).

Hekker et al. described freeze-dried smallpox vaccine compositions comprising pepton-sorbitol combinations with 2% haemaccel or 2% polyvinylpyrrolidone (Hekker et al. *Journal of Biological Standardization* 1973, 1: 21-32, summarized in Burke et al. *Crit Rev Ther Drug Carrier Syst* 1999, 16: 1-83). Further freeze-dried compositions comprising MVA or ALVAC are described in WO 03/053463, WO 05/066333, WO 07/056847, WO 2011/121306, WO 2014/053571, and Zhang et al. *Chemical Research in Chinese Universities* 2007, 23: 329-332. WO 2010/135495 describes methods for stabilizing viruses in a spray dry powder composition comprising mannitol.

Just and Finke analyzed lyophilized MVA compositions comprising stabilizers including albumin, sorbitol, dextran, cysteine or haemaccel and described 5% (w/v) sorbitol and 1% (w/v) human albumin superior for lyophilized compositions when stored at +4 degrees C. (Just and Finke *Zentralbl Bakteriol Orig A* 1979, 245: 276-282). They also analyzed stability for non-lyophilized MVA suspensions containing 1% (w/v) human albumin but a loss of virus titer was observed for these formulations when stored at −70 degrees C. over 8 months.

Prabhu et al. describe three freeze-dried vaccine formulations of camelpox (Prabhu et al. *Biologicals* 2014, 42: 169-175) one containing 3.5% hydrolyzed gelatin and 3.5% sorbitol in potassium phosphate buffer pH 6.2, which after reconstitution showed a loss in virus titer even at 4 degrees C.

Although freeze-dried vaccines are typically more heat-stable than non-lyophilized alternatives, lyophilization has some disadvantages, including costs, reconstitution before use, instability once reconstituted, and freezing and drying stress to the viral particles (Capelle et al. *Eur J Pharm Biopharm* 2018, 129: 215-221). Further, lyophilized vaccines are more prone to administration and dosing errors compared to liquid vaccines due to the need for reconstitution, which may lead to vaccine wastage or an ineffective vaccine dose (Capelle et al. *Eur J Pharm Biopharm* 2018, 129: 215-221).

There has also been an attempt to use vaccinia virus for oral vaccine application (U.S. Pat. No. 6,969,345). The compositions described comprise mannitol with other ingredients such as hydroxyethyl starch, fish oil, glycerol, and gelatin.

Moreover, liquid stabilization of live attenuated viral vaccines is the most challenging as degradation kinetics and dynamic processes are more favorable (Tlaxca et al. *Adv Drug Deliv Rev* 2015, 93: 56-78).

WO 2010/056991 describes liquid or liquid-frozen compositions comprising a MVA virus and mannitol, wherein mannitol is the sole stabilization agent of the composition.

A beneficial effect on poxvirus stability using a chelating agent and ethanol when stored e.g., at +5 degrees C. for 12 to 24 months is disclosed in WO 2016/087457.

WO 2011/121301 describes the use of N,N-dimethylglycine or N,N,N-trimethylglycine for stabilization of MVA in a liquid setting at 37 degrees C. for one week.

Amino acids are used as stabilizers in a wide range of applications, including antibodies, fusion proteins, and vaccine antigens (Maity & Goldstein; Maity & Davagnino;

Mistilis et. al.). In particular histidine or arginine are frequently used as stabilizers of various viral solutions and viral vaccines (Cardoso et. al.). For stabilizing viral vaccines in a liquid formulation histidine at a concentration of at least 5 mM, and preferably above 10 mM can be used for adenovirus-based vaccines (non-enveloped DNA virus) (Evans et. al.; WO2014/029702), whereas a life attenuated influenza vaccine (enveloped RNA virus) can be stabilized by arginine (White et. al.) in an at least concentration of 50 mM (US2007/0161085) or even in ranges up to 300 mM (WO2014/029702). Furthermore, in WO2014/029702 amino acids such as arginine and methionine were described as efficient stabilizers of four canine viruses (canine parvovirus, canine adenovirus type 2, canine distemper virus, canine parainfluenza virus).

However, there remains a need for new formulations allowing stabilization of poxvirus-based materials allowing large scale industrial applications, providing compositions for storage without affecting biological activity of the product and preserving desired characteristics of the virus, more particularly to avoid or reduce virus titer loss. There is in particular a need for liquid pharmaceutical poxvirus preparations that need not be stored below minus 60 degrees C. providing stability for extended periods of time. It is further desirable to provide high-titer low volume compositions suitable for storage at refrigerator temperature and/or at a temperature at about −20 degrees C.

In particular, a need remains for the development of a poxvirus liquid composition that is stable for approximately one year or longer at about −20 degrees C. followed by storage at +2 to +8 degrees C. (preferably for at least 6 or 9 months) and compatible with subcutaneous, intramuscular and/or intranasal administration. Also desirable are liquid poxvirus compositions that are stable for approximately one year or longer at +2 to +8 degrees C. Such liquid compositions offer advantages including lower cost of goods, decreased development and/or production time and convenience for the user. The present invention addresses and meets these needs by providing improved poxvirus compositions, in particular MVA compositions, which show enhanced storage stability.

BRIEF SUMMARY OF THE INVENTION

The present invention provides aqueous compositions with improved stability of a live poxvirus such as MVA.

Accordingly, in one aspect the present invention provides an aqueous composition having a pH of from pH 7.0 to pH 8.5 comprising:
- (a) arginine at a concentration of from 50 mM to 150 mM; or
- (b) albumin at a concentration of from 0.25% to 1.0% (w/v) or from 0.25% to less than 1.0% (w/v); or
- (c) gelatin at a concentration of from 1.0% to 3% (w/v) or from 1.0% to less than 3% (w/v).

Another aspect provides above composition further comprising a poxvirus, preferably MVA.

Another aspect provides above composition further comprising a poxvirus, preferably MVA, for use as a medicament or vaccine.

Another aspect provides the use of above composition for storing a poxvirus, preferably MVA.

Another aspect provides a method of preparing a composition further comprising a poxvirus, preferably MVA, comprising the steps of:

- (i) providing a preparation comprising a poxvirus, preferably MVA, in a pharmaceutically acceptable buffer, and
- (ii) combining the poxvirus preparation of step (i) with above composition.

BRIEF DESCRIPTION OF THE DRAWINGS

The accompanying drawings, which are incorporated in and constitute a part of this specification, illustrate several embodiments of the invention and together with the description serve to explain the principles of the invention.

DETAILED DESCRIPTION OF THE INVENTION

Figure 1:
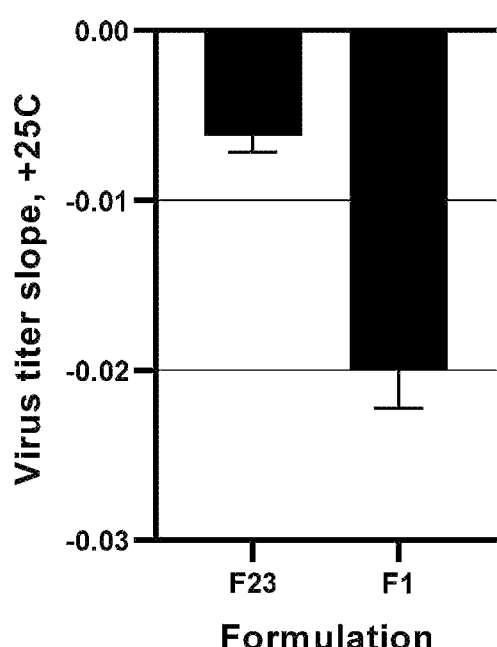
FIG. 1 shows virus titer slopes (change of MVA-BN-RSV titer over time, i.e. titer drop/day) for formulation F1 (10 mM Tris/140 mM NaCl) and formulation F23 (1% (w/v) rHSA, 3% (w/v) gelatin in 10 mM Tris/140 mM NaCl, 10% (w/v) sucrose, 2% (w/v) sorbitol). The virus titer slopes were calculated by means of linear regression analysis of virus titers determined at study start (time zero, t=0) and after 3 weeks (19 days) and 5 weeks (33 days) of incubation at +25 degrees Celsius. The error bars indicate the standard errors for each virus titer slope.

It was found previously by the inventors (PCT/EP2019/073825) that storage stability, including preserved biological function of MVA-BN-RSV, is provided by an aqueous composition of 10 mM Tris/140 mM NaCl containing 10% (w/v) sucrose, 2% (w/v) sorbitol, 1% (w/v) rHSA, and 3% (w/v) gelatin (herein referred to as formulation F23). Superior stability was observed in the aqueous composition having a pH ranging between pH 7.0 and pH 8.5.

However, rHSA is quite expensive and, therefore, would not be the pharmaceutical excipient of first choice when it comes to bulk production on a commercial scale. On the other hand, gelatin is an animal product and as such bears safety risks, e.g. the potential of transferring pathogenic agents. Additionally, there is a trend to avoid the animal products (e.g. veganism).

Therefore, a purpose of the study described herein was to investigate whether rHSA and/or gelatin concentrations could be reduced while maintaining their poxvirus stabilizing properties. Another purpose of the study was to investigate whether alternative excipients such as amino acids are capable of compensating for reduced concentrations of rHSA and/or gelatin.

In this study, different formulations containing MVA-BN-RSV were stored at "accelerated conditions", i.e. +25 degrees Celsius/60% relative humidity (RH), simulating "real time conditions" during an extended time period. Real time studies were initiated in parallel at +5° C. and −20° C. Additionally, freeze/thawing (F/T) experiments were carried out. The stability of MVA-BN-RSV was assessed based on a virus titer decrease and pH change.

The study yielded, inter alia, the following findings:

rHSA increases poxvirus stability. Maximum effect at 0.5% (w/v) rHSA; no difference between 0.5% (w/v) rHSA and 1.0% (w/v) rHSA.

Gelatin (in the presence of rHSA) increases poxvirus stability.

Maximum effect at 1.5% (w/v) gelatin; no difference between 1.5% (w/v) and 3% (w/v) gelatin.

Arginine (100 mM) increases poxvirus stability. Thus, arginine is capable of compensating for reduced concentrations of rHSA and/or gelatin. Moreover, arginine can replace rHSA and gelatin

Preferred Embodiments

In one embodiment, the composition comprising arginine comprises arginine at a concentration of from 75 mM to 125 mM, preferably 80 mM to 120 mM, more preferably 90 mM to 110 mM, even more preferably 95 mM to 105 mM, most preferably 100 mM.

In one embodiment, the composition comprising albumin comprises albumin at a concentration of from 0.3% to less than 1.0% (w/v), preferably 0.4% to less than 1% (w/v), most preferably 0.5% to less than 1% (w/v).

In one embodiment, the composition comprising albumin comprises albumin at a concentration of from 0.25% to 0.9% (w/v), preferably 0.3% to 0.7% (w/v), more preferably 0.4% to 0.6% (w/v), most preferably 0.5% (w/v).

In one embodiment, the composition comprising gelatin comprises gelatin at a concentration of from 1.0% to 2% (w/v), more preferably 1.5% to 2% (w/v) most preferably 1.5 (w/v).

In one embodiment, the composition comprising albumin additionally comprises gelatin.

In one embodiment, the composition comprises 0.1% (w/v) albumin and 1.5% (w/v) gelatin or 0.25% (w/v) albumin and 1.5% (w/v) gelatin.

In one embodiment, the composition further comprises a pharmaceutically acceptable buffer, preferably Tris buffer, more preferably 10 mM Tris buffer.

In one embodiment, the composition further comprises a pharmaceutically acceptable salt, preferably sodium chloride, most preferably 140 mM sodium chloride.

In one embodiment, the composition further comprises a disaccharide, preferably sucrose, most preferably 10% (w/v) sucrose.

In one embodiment, the composition further comprises sorbitol, most preferably 2% (w/v) sorbitol.

In one embodiment, the composition comprises arginine at a concentration of from 50 mM to 150 mM, Tris buffer and sodium chloride, and preferably is free of a chelating agent and/or glutamic acid. Optionally, the composition further comprises sucrose and sorbitol.

In one embodiment, the composition is used for storing the poxvirus for at least 2 years at −50 degrees Celsius or −20 degrees Celsius.

In one embodiment, the composition is used for storing the poxvirus for at least 6 months at +5 degrees Celsius or +20 degrees Celsius.

In one embodiment of the composition, the use or the method, the poxvirus is an orthopoxvirus, more preferably a vaccinia virus, even more preferably a modified vaccinia virus Ankara (MVA), most preferably MVA-BN®.

In one embodiment of the composition, the use or the method, the poxvirus is a recombinant poxvirus, most preferably a recombinant MVA, encoding at least one respiratory syncytial virus (RSV) protein or a part thereof.

In one embodiment, the composition (with or without poxvirus) is according to any of formulations F23 and F69 to F80 as defined in Table 1.

In one embodiment, the composition (with or without poxvirus) comprises rHSA and gelatin at concentrations as any of the formulations defined in Table 1A.

In one embodiment, the composition (with or without poxvirus) comprises rHSA at a concentration as any of the formulations defined in Table 1B.

In one embodiment, the composition (with or without poxvirus comprises rHSA and albumin at concentrations of any of the formulations defined in Table 1C.

In one embodiment, the composition (with or without poxvirus) comprises rHSA, gelatin and arginine at concentrations as defined in Table 1D.

Poxvirus

Poxviruses are large viruses that are generally enveloped viruses and carry double-stranded DNA. Poxviruses belong to the Poxviridae family and include 71 species of viruses which are divided among 16 genera (Virus Taxonomy: 2017 Release). Two of the most well-known orthopoxviruses are the variola virus, the causative agent for small pox, and vaccinia virus, whose conversion to a vaccine enabled the eradication of smallpox.

Poxviruses, such as a vaccinia virus, are known to the skilled person and have been used to generate recombinant vaccines in the fight against infectious organisms and more recently cancers (Mastrangelo et al. *J Clin Invest* 2000, 105: 1031-1034).

Within the context of present disclosure, poxviruses preferably include orthopoxviruses or avipoxviruses. In preferred embodiments of the present invention, the poxvirus is an orthopoxvirus.

Orthopoxviruses include, but are not limited to, variola virus, vaccinia virus, cowpox virus, and monkeypox virus. Preferably, the orthopoxvirus is a vaccinia virus.

The term "vaccinia virus" can refer to the various strains or isolates of replicating vaccinia virus (VACV) including, for example, Ankara, VACV Western Reserve (WR), VACV Copenhagen (VACV-COP), Temple of Heaven, Paris, Budapest, Dairen, Gam, MRIVP, Per, Tashkent, TBK, Tian Tan, Tom, Bern, Patwadangar, BIEM, B-15, EM-63, IHD-J, IHD-W, Ikeda, DryVax (also known as VACV Wyeth or New York City Board of Health [NYCBH] strain), NYVAC, ACAM1000, ACAM2000, Vaccinia Lister (also known as Elstree), LC16mO or LC16m8.

In further embodiments, the poxvirus of the invention is an MVA virus.

MVA virus was generated by 516 serial passages on chicken embryo fibroblasts of the Ankara strain of vaccinia virus (CVA) (for review see Mayr et al. *Infektion* 1975, 3: 6-14). As a consequence of these long-term passages, the genome of the resulting MVA virus had about 31 kilobases of its genomic sequence deleted and, therefore, was described as highly host cell restricted for replication to avian cells (Meyer et al. *J Gen Virol* 1991, 72 (Pt 5): 1031-1038). It was shown in a variety of animal models that the resulting MVA was significantly avirulent compared to the fully replication competent starting material (Mayr and Danner *Dev Biol Stand* 1978, 41: 225-234).

An MVA virus useful in the practice of the present invention can include, but is not limited to, MVA-572 (deposited as ECACC V94012707 on Jan. 27, 1994); MVA-575 (deposited as ECACC V00120707 on Dec. 7, 2000), MVA-1721 (referenced in Suter et al. *Vaccine* 2009, 27: 7442-7450), NIH clone 1 (deposited as ATCC® PTA-5095 on Mar. 27, 2003) and MVA-BN (deposited at the European Collection of Cell Cultures (ECACC) under number V00083008 on Aug. 30, 2000).

More preferably the MVA used in accordance with the present invention includes MVA-BN and MVA-BN derivatives. MVA-BN has been described in International PCT publication WO 02/042480. "MVA-BN derivatives" refer to any virus exhibiting essentially the same replication characteristics as MVA-BN, as described herein, but exhibiting differences in one or more parts of their genomes.

MVA-BN, as well as MVA-BN derivatives, is replication incompetent, meaning a failure to reproductively replicate in vivo and in vitro. More specifically in vitro, MVA-BN or MVA-BN derivatives have been described as being capable of reproductive replication in chicken embryo fibroblasts (CEF), but not capable of reproductive replication in the human keratinocyte cell line HaCat (Boukamp et al (1988), *J. Cell Biol.* 106:761-771), the human bone osteosarcoma cell line 143B (ECACC Deposit No. 91112502), the human embryo kidney cell line 293 (ECACC Deposit No. 85120602), and the human cervix adenocarcinoma cell line HeLa (ATCC Deposit No. CCL-2). Additionally, MVA-BN or MVA-BN derivatives have a virus amplification ratio at least two-fold less, more preferably three-fold less than MVA-575 in Hela cells and HaCaT cell lines. Tests and assay for these properties of MVA-BN and MVA-BN derivatives are described in WO 02/42480 (U.S. Patent application No. 2003/0206926) and WO 03/048184 (U.S. Patent application No. 2006/0159699).

The term "not capable of reproductive replication" or "no capability of reproductive replication" in human cell lines in vitro as described in the previous paragraphs is, for example, described in WO 02/42480, which also teaches how to obtain MVA having the desired properties as mentioned above. The term applies to a virus that has a virus amplification ratio in vitro at 4 days after infection of less than 1 using the assays described in WO 02/42480 or in U.S. Pat. No. 6,761,893.

The term "failure to reproductively replicate" refers to a virus that has a virus amplification ratio in human cell lines in vitro as described in the previous paragraphs at 4 days after infection of less than 1. Assays described in WO 02/42480 or in U.S. Pat. No. 6,761,893 are applicable for the determination of the virus amplification ratio.

The amplification or replication of a virus in human cell lines in vitro as described in the previous paragraphs is normally expressed as the ratio of virus produced from an infected cell (output) to the amount originally used to infect the cell in the first place (input) referred to as the "amplification ratio". An amplification ratio of "1" defines an amplification status where the amount of virus produced from the infected cells is the same as the amount initially used to infect the cells, meaning that the infected cells are permissive for virus infection and reproduction. In contrast, an amplification ratio of less than 1, i.e., a decrease in output compared to the input level, indicates a lack of reproductive replication and therefore attenuation of the virus.

In another embodiment, the poxvirus of the present invention is an avipoxvirus, such as (but not limited to) a fowlpox virus.

The term "avipoxvirus" refers to any avipoxvirus, such as Fowlpoxvirus, Canarypoxvirus, Uncopoxvirus, Mynahpoxvirus, Pigeonpoxvirus, Psittacinepoxvirus, Quailpoxvirus, Peacockpoxvirus, Penguinpoxvirus, Sparrowpoxvirus, Starlingpoxvirus and Turkeypoxvirus. Preferred avipoxviruses are Canarypoxvirus and Fowlpoxvirus.

Avipoxvirus is a genus of Poxviridae whose viruses are able to infect and replicate in birds, however are unable to replicate in non-avian species (Vanderplasschen and Pastoret *Curr Gene Ther* 2003, 3: 583-595). Avipoxviruses, such as fowlpox virus, have been shown to be a safe and efficacious non-replicating vector when used in non-avian species. Id.

An example of a canarypox virus is strain Rentschler. A plaque purified Canarypox strain termed ALVAC (U.S. Pat. No. 5,766,598) was deposited under the terms of the Budapest treaty with the American Type Culture Collection (ATCC), accession number VR-2547. Another Canarypox strain is the commercial canarypox vaccine strain designated LF2 CEP 524 24 10 75, available from Institute Merieux, Inc.

Examples of a Fowlpox virus are strains FP-1, FP-5, TROVAC (U.S. Pat. No. 5,766,598), PDXVAC-TC (U.S. Pat. No. 7,410,644), TBC-FPV (Therion Biologics—FPV). FP-1 is a Duvette strain modified to be used as a vaccine in one-day old chickens. The strain is a commercial fowlpox virus vaccine strain designated O DCEP 25/CEP67/239 October 1980 and is available from Institute Merieux, Inc. FP-5 is a commercial fowlpox virus vaccine strain of chicken embryo origin available from American Scientific Laboratories (Division of Schering Corp.) Madison, Wis., United States Veterinary License No. 165, serial No. 30321.

In another embodiment, the poxvirus or any of the preferred poxviruses of any of the embodiments of the present invention is a live virus.

The poxvirus (in particular the orthopoxvirus, more particular a vaccinia virus or preferably MVA) is preferably present in the aqueous compositions of the present invention at a titer of at least $10^7$ InfU/mL, preferably of at least $2\times10^7$ InfU/mL, at least $3\times10^7$ InfU/mL, at least $5\times10^7$ InfU/mL, at least $6\times10^7$ InfU/mL, at least $7\times10^7$ InfU/mL, at least $8\times10^7$ InfU/mL, at least $9\times10^7$ InfU/mL, at least $1\times10^8$ InfU/mL, at least $2\times10^8$ InfU/mL, at least $3\times10^8$ InfU/mL, at least $4\times10^8$ InfU/mL, at least $5\times10^8$ InfU/mL, at least $6\times10^8$ InfU/mL, at least $7\times10^8$ InfU/mL, at least $8\times10^8$ InfU/mL, at least $9\times10^8$ InfU/mL, at least $1\times10^9$ InfU/mL, at least $2\times10^9$ InfU/mL, at least $3\times10^9$ InfU/mL, at least $4\times10^9$ InfU/mL, at least $5\times10^9$ InfU/mL, at least $6\times10^9$ InfU/mL, or at least $7\times10^9$ InfU/mL.

For practical reasons, the poxvirus (in particular the orthopoxvirus, more particular a vaccinia virus or preferably MVA) is present in the aqueous compositions of the present invention at a titer of at most $1\times10^{11}$ InfU/mL, at most $5\times10^{10}$ InfU/mL, or preferably at most $1\times10^{10}$ InfU/mL.

In particular, the poxvirus (in particular the orthopoxvirus, more particular a vaccinia virus or preferably MVA) is present in the aqueous compositions of the present invention at a titer of between about $1\times10^{7}$ InfU/mL to $1\times10^{11}$ InfU/mL.

In particular, the poxvirus (in particular the orthopoxvirus, more particular a vaccinia virus or preferably MVA) is present in the aqueous compositions of the present invention at a titer of between about $1\times10^{7}$ InfU/mL to $5\times10^{10}$ InfU/mL.

In particular, the poxvirus (in particular the orthopoxvirus, more particular a vaccinia virus or preferably MVA) is present in the aqueous compositions of the present invention at a titer of between about $1\times10^{7}$ InfU/mL to $1\times10^{10}$ InfU/mL.

In particular, the poxvirus (in particular the orthopoxvirus, more particular a vaccinia virus or preferably MVA) is present in the aqueous compositions of the present invention at a titer of between about $1\times10^{7}$ InfU/mL to $6\times10^{9}$ InfU/mL.

In certain embodiments, the aqueous compositions provided herein are administered to the subject in a single dose, or in multiple (i.e., 2, 3, 4, etc.) doses, preferably in a volume of 0.1 to 0.5 ml. In certain embodiments, the aqueous compositions provided herein are administered to the subject in a dose of $10^{7}$ to $10^{10}$ InfU of the virus in the aqueous composition, preferably in a volume of 0.1 to 0.5 ml. In certain other embodiments, the aqueous compositions are administered in a first (priming) inoculation and one or more subsequent boosting administrations. In certain embodiments, the first dose comprises $10^{7}$ to $10^{10}$ InfU of the poxvirus in the aqueous composition and the second dose comprises $10^{7}$ to $10^{10}$ InfU of the virus of the aqueous composition, preferably in a volume of 0.1 to 0.5 ml.

In certain embodiments, the one or more subsequent boosting administrations comprise the same recombinant poxvirus as previously administered, and the methods comprise a homologous prime-boost vaccination. In certain embodiments, the one or more subsequent boosting administrations comprise a different recombinant poxvirus than previously administered, and the methods comprise a heterologous prime-boost vaccination.

In certain embodiments, the one or more subsequent administrations (i.e., the one or more boosting vaccinations) are administered at intervals comprising days, weeks or months after administration of the initial priming vaccination. In certain embodiments, the one or more subsequent administrations of a recombinant poxvirus (i.e., the one or more boosting vaccinations) are administered at intervals of 1, 2, 3, 4, 5, 6, 7 or more weeks after administration of the initial amount of a recombinant poxvirus (i.e., the priming vaccination). In certain embodiments, the one or more subsequent administrations of a recombinant poxvirus (i.e., the one or more boosting vaccinations) are administered at intervals of 1, 2, 3, 4, 5, 6, 7, 8, 9, 10, 11, 12 or more months after administration of the initial priming vaccination.

The poxvirus (in particular the orthopoxvirus, more particular a vaccinia virus or preferably MVA) comprised in the compositions of the present invention may be a wild-type poxvirus, an attenuated poxvirus or a recombinant poxvirus.

The term "recombinant" virus of any of the embodiments as described herein refers to a virus, more particularly a poxvirus, comprising an exogenous nucleic acid sequence inserted in its genome, which is not naturally present in the parent virus. A recombinant virus (e.g., in particular the orthopoxvirus, more particular a vaccinia virus or preferably MVA), thus refers to a virus made by an artificial combination of two or more segments of nucleic acid sequence of synthetic or semisynthetic origin which does not occur in nature or is linked to another nucleic acid in an arrangement not found in nature. The artificial combination is most commonly accomplished by artificial manipulation of isolated segments of nucleic acids, using well-established genetic engineering techniques. Generally, a "recombinant" poxvirus as described herein refers to a poxvirus that is produced by standard genetic engineering methods, e.g., a MVA virus of the present invention is thus a genetically engineered or a genetically modified MVA virus. The term "recombinant MVA" thus includes a MVA virus (e.g., MVA-BN) which has integrated at least one recombinant nucleic acid, preferably in the form of a transcriptional unit, in its genome. A transcriptional unit may include a promoter, enhancer, terminator and/or silencer. Recombinant MVA viruses of the present invention may express heterologous antigenic determinants, polypeptides or proteins (antigens) upon induction of the regulatory elements e.g., the promoter.

Methods for Production of Recombinant Poxviruses

Methods to obtain recombinant poxviruses (e.g., VACV or MVA) or to insert exogenous coding sequences into a poxvirus (e.g., VACV or MVA) genome are well known to the person skilled in the art. For example, methods for standard molecular biology techniques such as cloning of DNA, DNA and RNA isolation, Western blot analysis, RT-PCR and PCR amplification techniques are described in Molecular Cloning, A laboratory Manual $2^{nd}$ Ed. (J. Sambrook et al., Cold Spring Harbor Laboratory Press (1989)), and techniques for the handling and manipulation of viruses are described in Virology Methods Manual (B. W. J. Mahy et al. (eds.), *Academic Press* (1996)). Similarly, techniques and know-how for the handling, manipulation and genetic engineering of poxviruses are described in Molecular Virology: A Practical Approach (A. J. Davison & R. M. Elliott (Eds.), The Practical Approach Series, IRL Press at Oxford University Press, Oxford, UK (1993), see, e.g., Chapter 9: Expression of genes by Vaccinia virus vectors); Current Protocols in Molecular Biology (John Wiley & Son, Inc. (1998), see, e.g., Chapter 16, Section IV: Expression of proteins in mammalian cells using vaccinia viral vector); and Genetic Engineering, Recent Developments in Applications, Apple Academic Press (2011), Dana M. Santos, see, e.g., Chapter 3: Recombinant-mediated Genetic Engineering of a Bacterial Artificial Chromosome Clone of Modified Vaccinia Virus Ankara (MVA)). Construction and isolation of recombinant MVA are also described in Methods and Protocols, Vaccinia Virus and Poxvirology, ISBN 978-1-58829-229-2 (Staib et al.), Humana Press (2004) see, e.g., Chapter 7.

Methods for producing larger amounts of recombinant poxvirus and purifying virus-based material such as viral vectors and/or viruses used according to the present invention are known by the person skilled in the art. Available methods comprise the replication of the virus in CEF cells or cell lines in particular DF-1 (U.S. Pat. No. 5,879,924), EBx chicken cell line (WO 2005/007840), EB66 duck cells (WO 08/129058), or Cairina *moschata* immortalized avian cells (WO 2007/077256 or WO 2009/004016). They can be cultivated under conditions well known to the person skilled in the art. Serum-free methods for virus cultivation and virus amplification are preferred. Particulary, serum-free methods for virus cultivation and virus amplification in CEF cells are described for example in WO 2004/022729. Upstream and downstream processes for production of virus are well known to the skilled person. They may be obtained from WO 2012/010280 or WO 2016/087457. Methods as useful for purifying viruses of the present application are disclosed in WO 03/054175, WO 07/147528, WO 2008/138533, WO 2009/100521 and WO 2010/130753. Exemplary methods for propagation and purification of recombinant poxvirus in duck embryo-derived cell are described in Leon et al. *Vaccine* 2016, 34: 5878-5885.

Exemplary Generation of a Recombinant MVA Virus

For the generation of the various recombinant MVA viruses disclosed herein, different methods may be applicable. The DNA sequence to be inserted into the virus can be placed into an *E. coli* plasmid construct into which DNA homologous to a section of DNA of the poxvirus has been inserted. Separately, the DNA sequence to be inserted can be ligated to a promoter. The promoter-gene linkage can be positioned in the plasmid construct so that the promoter-gene linkage is flanked on both ends by DNA homologous to a DNA sequence flanking a region of poxvirus DNA containing a non-essential locus. The resulting plasmid construct can be amplified by propagation within *E. coli* bacteria and isolated. The isolated plasmid containing the DNA gene sequence to be inserted can be transfected into a cell culture, e.g., of chicken embryo fibroblasts (CEFs), at the same time the culture is infected with MVA virus. Recombination between homologous MVA viral DNA in the plasmid and the viral genome, respectively, can generate a poxvirus modified by the presence of foreign DNA sequences.

According to a preferred embodiment, a cell of a suitable cell culture as, e.g., CEF cells, can be infected with an MVA virus. The infected cell can be, subsequently, transfected with a first plasmid vector comprising a foreign or heterologous gene or genes, such as one or more of the nucleic acids provided in the present disclosure; preferably under the transcriptional control of a poxvirus expression control element. As explained above, the plasmid vector also comprises sequences capable of directing the insertion of the exogenous sequence into a selected part of the MVA viral genome. Optionally, the plasmid vector also contains a cassette comprising a marker and/or selection gene operably linked to a poxvirus promoter. The use of selection or marker cassettes simplifies the identification and isolation of the generated recombinant poxvirus. However, a recombinant poxvirus can also be identified by PCR technology. Subsequently, a further cell can be infected with the recombinant poxvirus obtained as described above and transfected with a second vector comprising a second foreign or heterologous gene or genes. In case, this gene shall be introduced into a different insertion site of the poxvirus genome, the second vector also differs in the poxvirus-homologous sequences directing the integration of the second foreign gene or genes into the genome of the poxvirus. After homologous recombination has occurred, the recombinant virus comprising two or more foreign or heterologous genes can be isolated. For introducing additional foreign genes into the recombinant virus, the steps of infection and transfection can be repeated by using the recombinant virus isolated in previous steps for infection and by using a further vector comprising a further foreign gene or genes for transfection.

In other embodiments, the recombinant poxvirus (in particular the orthopoxvirus, more particular a vaccinia virus or preferably MVA) of any of the embodiments of the present invention comprises a nucleic acid encoding an antigen, preferably at least one antigen.

Suitable antigens according to the invention for instance may include one or more transgene(s) with an open reading frame encoding for one or more polypeptide(s) against which an immune response is desired when the virus is used for vaccination purposes. Examples may include for instance a transgene or several transgenes suitable to generate an immune response against a virus or a pathogen including but not limited to RSV, HIV, HPV, HBV, Malaria, Ebola, MARV, FMDV, Dengue, an Equine encephalitis virus or any combination thereof.

In a preferred embodiment, the antigen is a viral antigen, a costimulatory molecule and/or a Tumor Associated antigen (TAA).

In preferred embodiments of the present invention, the viral antigen is an immunogenic antigen selected from a filovirus, a picornavirus, a papillomavirus, a hepatitis virus, a flavivirus, a retrovirus, an orthomyxovirus, an equine encephalitis virus, a paramyxovirus, and/or a combination thereof.

In preferred embodiments of the present invention, the immunogenic antigen is a protein, preferably a full-length protein.

In a preferred embodiment of the invention, the paramyxovirus is a respiratory syncytial virus (RSV) e.g., as described in WO 2014/019718.

In another preferred embodiment, the recombinant poxvirus (in particular the orthopoxvirus, more particular a vaccinia virus or preferably MVA) of any of the embodiments of the present invention comprises a nucleic acid encoding a RSV antigen.

In another preferred embodiment, the recombinant poxvirus (in particular the orthopoxvirus, more particular a vaccinia virus or preferably MVA) of any of the embodiments comprises a nucleic acid encoding a RSV protein.

In another preferred embodiment, the recombinant poxvirus (in particular the orthopoxvirus, more particular a vaccinia virus or preferably MVA) of any of the embodiments comprises a nucleic acid encoding a RSV F glycoprotein.

In another preferred embodiment, the recombinant poxvirus (in particular the orthopoxvirus, more particular a vaccinia virus or preferably MVA) of any of the embodiments comprises a nucleic acid encoding a RSV F glycoprotein and a RSV G glycoprotein.

In another preferred embodiment, the recombinant poxvirus (in particular the orthopoxvirus, more particular a vaccinia virus or preferably MVA) of any of the embodiments comprises a nucleic acid encoding a RSV F glycoprotein and two RSV G glycoproteins.

In another preferred embodiment, the recombinant poxvirus (in particular the orthopoxvirus, more particular a vaccinia virus or preferably MVA) of any of the embodiments comprises a nucleic acid encoding a RSV F glycoprotein, two RSV G glycoproteins and a RSV N protein.

In another preferred embodiment, the recombinant poxvirus (in particular the orthopoxvirus, more particular a vaccinia virus or preferably MVA) of any of the embodiments comprises a nucleic acid encoding a RSV F glycoprotein, two RSV G glycoproteins, a RSV N protein and a RSV matrix protein.

In another preferred embodiment, the recombinant poxvirus (in particular the orthopoxvirus, more particular a vaccinia virus or preferably MVA) of any of the embodiments comprises a nucleic acid encoding a RSV F glycoprotein, two RSV G glycoproteins, a RSV N protein and a RSV M2-1 protein.

In a preferred embodiment of the invention, the filovirus is an Ebolavirus and/or a Marburg virus (MARV) e.g., as described in WO 2016/036955, WO 2016/036971 or WO 2016/034678.

In a preferred embodiment of the invention, the picornavirus is a Foot and Mouth disease virus (FMDV) e.g., as described in WO 2016/202828.

In a preferred embodiment of the invention, the papillomavirus is a human papilloma virus e.g., as described in WO 2017/192418, WO 90/10459, WO 05/09241, WO 98/04705, WO 99/03885 or WO 2007/121894.

In a preferred embodiment of the invention, the hepatitis virus is selected from the group of hepatitis A virus, hepatitis B virus, a hepatitis C virus and hepatitis E virus e.g., as described in WO 2004/111082.

In a preferred embodiment of the invention, the flavivirus is a dengue virus (DENV).

In a preferred embodiment of the invention, the retrovirus is HIV-1.

In a preferred embodiment of the invention, the orthomyxovirus is an influenza virus.

In a preferred embodiment of the invention, the equine encephalitis virus (EEV) is an eastern equine encephalitis virus (EEEV), western equine encephalitis virus (WEEV) and/or Venezuelan equine encephalitis virus (VEEV) e.g., as described in WO 2017/129765.

In preferred embodiments of the present invention, the viral antigen is an immunogenic antigen selected from the group of RSV, Ebola virus, MARV, FMDV, HPV, HBV, HIV, influenza virus, DENV, RSV, EEV and any combination thereof.

Various costimulatory molecules are known to the skilled person. They include but are not limited to ICAM-1, LFA-3, CD72, B7-1, B7-2, CD40, CD40 ligand (CD40L) or other B7 related molecules or combinations thereof such as TRICOM.

"TRICOM." Triad of Costimlatory Molecules (also known as TRICOM) includes B7-1 (also known as B7.1 or CD80), intracellular adhesion molecule-1 (ICAM-1, also known as CD54) and lymphocyte function-associated antigen-3 (LFA-3, also known as CD58), and is commonly included in recombinant viral vectors (e.g., poxviral vectors) expressing a specific antigen in order to increase the antigen-specific immune response. The individual components of TRICOM can be under the control of the same or different promoter(s) and can be provided on the same vector with the specific antigen or on a separate vector. Exemplary vectors are disclosed, for example, in Hodge et al. *Cancer Res* 1999, 59: 5800-5807 et al., "A Triad of Costimulatory Molecules Synergize to Amplify T-Cell Activation," Cancer Res. 59:5800-5807 (1999) and U.S. Pat. No. 7,211,432 B2, both of which are incorporated herein by reference.

A TAA is well known to the skilled person and refers to an autologous cellular antigen detected at a higher frequency or density in tumor tissue or on tumor cells compared to non-tumor tissue or non-tumor cells.

In a preferred embodiment, the TAA is selected from the group of CEA, MUC-1, TRP-1, NY-ESO-1, TRP-2, p53, PSA, HER-2, PAP, survivin, TYRP1, TYRP2, or Brachyury or in any combination thereof.

In other embodiments, the recombinant poxvirus (in particular the orthopoxvirus, more particular a vaccinia virus or preferably MVA) of any of the embodiments of the present invention comprises a nucleic acid encoding a combination of TAAs. Such exemplary combination may include HER2 and Brachyury, CEA and MUC-1, or PAP and PSA.

Sucrose and Sorbitol

The aqueous composition according to the present invention contain sucrose disaccharide. Alternative disaccharides may be considered, e.g. trehalose or a combination of sucrose and trehalose.

In certain embodiments, the aqueous compositions according to the invention comprise the disaccharide (preferably sucrose) at a concentration ranging between 2% (w/v) and 12% (w/v), preferably between 4% (w/v) and 12% (w/v). In particular, the aqueous compositions according to the invention comprises the disaccharide (preferably sucrose) at a concentration is-ranging between 2% (w/v) and 11% (w/v), between 2% (w/v) and 10% (w/v), between 2% (w/v) and 9% (w/v), between 2% (w/v) and 8% (w/v), between 2% (w/v) and 7% (w/v), between 2% (w/v) and 6% (w/v), between 2% (w/v) and 5% (w/v), between 4% (w/v) and 12% (w/v), between 4% (w/v) and 11% (w/v), between 4% (w/v) and 10% (w/v), between 4% (w/v) and 9% (w/v), between 4% (w/v) and 8% (w/v), between 4% (w/v) and 7% (w/v), between 5% (w/v) and 12% (w/v), between 5% (w/v) and 11% (w/v), between 5% (w/v) and 10% (w/v), between 5% (w/v) and 9% (w/v), between 5% (w/v) and 8% (w/v), between 6% (w/v) and 12% (w/v), between 6% (w/v) and 11% (w/v), between 6% (w/v) and 10% (w/v), between 6% (w/v) and 9% (w/v), between 6% (w/v) and 8% (w/v), between 7% (w/v) and 12% (w/v), between 7% (w/v) and 11% (w/v), between 7% (w/v) and 10% (w/v), between 7% (w/v) and 9% (w/v), or between 7% (w/v) and 8% (w/v).

In other embodiments, the aqueous compositions according to the invention comprise sucrose at a concentration ranging between 4% (w/v) and 12% (w/v).

In other embodiments, the aqueous compositions according to the invention comprise sucrose at a concentration of 10% (w/v).

Furthermore, the aqueous compositions according to the invention comprise sorbitol.

In certain embodiments, the aqueous compositions according to the invention comprise sorbitol at a concentration ranging between 0.2% (w/v) and 5% (w/v).

In other embodiments, the aqueous compositions according to the invention comprises sorbitol at a concentration ranging between 0.2% (w/v) and 4% (w/v).

In other embodiments, the aqueous compositions according to the invention comprise sorbitol at a concentration ranging between 0.5% (w/v) and 4% (w/v), preferably at a concentration ranging between 0.5% (w/v) and 3% (w/v).

In other embodiments, the aqueous compositions according to the invention comprise sorbitol at a concentration ranging between 0.2% (w/v) and 2.2% (w/v), preferably at a concentration ranging between 0.5% (w/v) and 2.2% (w/v).

In other embodiments, the aqueous compositions according to the invention comprise sorbitol at a concentration ranging between 1% (w/v) and 4% (w/v), preferably at a concentration ranging between 1% (w/v) and 3% (w/v).

In other embodiments, the aqueous compositions according to the invention comprise sorbitol at a concentration of 2% (w/v).

In other embodiments, the aqueous compositions according to the invention comprise sorbitol at a concentration of 2% (w/v).

Gelatin

Gelatin as used for the present invention is well known to a skilled person. Gelatin is a natural, water-soluble protein, gelling or non-gelling, which may be obtained by the partial hydrolysis of collagen produced from bones, hides and skins, tendons and sinews of animals including pig, cow, fish, and poultry. Whereas type A gelatin is produced by an acid processing of collagenous raw materials, type B is produced by the alkaline processing of collagenous raw materials. As gelatin for pharmaceutical preparations, there can be mentioned, for example, a purified gelatin described in the European Pharmacopoeia (Ph.Eur.) or U.S. Pharmacopoeia (USP).

The term "gelatin hydrolysate" according to the present invention is also called hydrolyzed gelatin, hydrolyzed collagen, collagen hydrolysate, collagen peptide, gelatine hydrolysate and hydrolyzed gelatine. The terms can be used interchangeable.

The terminology "gelatin hydrolysate" means either a hydrolyzed polypeptide obtained by subjecting gelatin to degradation through hydrolytic cleavage or a polypeptide obtained by polymerizing the above-mentioned hydrolyzed polypeptides. Gelatin hydrolysate is water-soluble and has preferably has a molecular weight of about 35,000 or less. As illustrative examples of gelatin usable in the present invention, there can be mentioned commercially available products, such as VacciPro® (tradename of hydrolyzed gelatin or chemical derivative thereof manufactured and sold by Gelita®, AG, Germany), Gelysate® (tradename of hydrolyzed gelatin or chemical derivative thereof manufactured and sold by BBL Co., Ltd., USA), and Rousselot® pharmaceutical gelatin (tradename of hydrolyzed gelatin or chemical derivative thereof manufactured and sold by Rousselot B.V, NL).

In other embodiments, the gelatin of the aqueous compositions of the invention is preferably bovine or porcine gelatin, preferably porcine or bovine gelatin hydrolysate. Porcine gelatin is preferably used.

In other embodiments of the present invention, the gelatin is porcine type A gelatin. In other embodiments of the present invention, the gelatin is porcine type B gelatin.

In other embodiments, the aqueous compositions of the invention comprise gelatin or gelatin hydrolysate or any of the preferred gelatin at a concentration from between about 0.02% (w/v) and 5% (w/v). In further embodiments the aqueous compositions of the invention comprise gelatin or gelatin hydrolysate or any of the preferred gelatin at a concentration from between about 0.1% (w/v) and 5% (w/v). In other embodiments, the aqueous compositions of the invention comprise gelatin or gelatin hydrolysate or any of the preferred gelatin at a concentration from between about 0.2% (w/v) and 5% (w/v). In other embodiments, the aqueous compositions of the invention comprise gelatin or gelatin hydrolysate or any of the preferred gelatin at a concentration from between about 0.25% (w/v) and 5% (w/v). In other embodiments, the aqueous compositions of the invention comprise gelatin or gelatin hydrolysate or any of the preferred gelatin at a concentration from between about 0.25% (w/v) and 4% (w/v). In other embodiments, the aqueous compositions of the invention comprise gelatin or gelatin hydrolysate or any of the preferred gelatin at a concentration from between about 0.2% (w/v) and 3.2% (w/v). In other embodiments, the aqueous compositions of the invention comprise gelatin or gelatin hydrolysate or any of the preferred gelatin at a concentration from between about 1% (w/v) and 3.2% (w/v), preferably 2.5% (w/v) and 3% (w/v). In other embodiments, the aqueous compositions of the invention comprise gelatin or gelatin hydrolysate or any of the preferred gelatin at a concentration of 0.25% (w/v), 0.5% (w/v), 1% (w/v), 1.5% (w/v), 2% (w/v), or 3% (w/v).

In one embodiment, the aqueous composition comprises Tris buffer, sodium chloride, sucrose, sorbitol, and arginine, but no added gelatin.

Serum Albumin

In other embodiments, the aqueous compositions according to the invention comprise albumin. Albumin is a protein naturally found in the blood plasma of mammals where it is the most abundant protein. It has important roles in maintaining the desired osmotic pressure of the blood and also in transport of various substances in the blood stream. The albumin used for the present invention is preferably a human, pig, mouse, rat, rabbit or goat albumin but also includes variants such as described in WO 2011/051489, WO 2011/051489, WO2010/092135, WO 2012/150319, WO 2014/072481, WO 2011124718, WO 2015/036579, WO 2018/065491, WO 2017/029407, WO 2013/075066, or Otagiri and Chuang *Biol Pharm Bull* 2009, 32: 527-534. Those skilled in the art will also recognize that modifications can be made to albumin by any means known in the art, for example, by recombinant DNA technology, by posttranslational modification, by proteolytic cleavage and/or by chemical means. Those substitutions and alterations to albumin that provide essentially equivalent stabilizing function to albumin without substitutions or alterations are contemplated herein. Preferably the albumin is human serum albumin. In other embodiments, the albumin is a recombinant albumin, preferably a recombinant human serum albumin (rHSA) expressed and purified from *Pichia pastoris, Saccharomyces cerevisiae* or *Oryza sativa*. Preferably the albumin as used according to the present invention is Recombumin® expressed in *Saccharomyces cerevisiae*. However, other recombinant albumins are suitable for the present invention such as for example human recombinant albumin expressed in *Pichia pastoris* (e.g. Albagen™, rHSA, CAS number 70024-90-7, Sigma-Aldrich).

In other embodiments, the aqueous compositions according to the invention comprise albumin (preferably any of the preferred albumins mentioned herein) at a concentration ranging between 0.02% (w/v) and 3% (w/v), preferably at a concentration ranging between 0.02% (w/v) and 2% (w/v).

In other embodiments, the aqueous compositions according to the invention comprise albumin (preferably any of the preferred albumins mentioned herein) at a concentration ranging between 0.2% (w/v) and 2% (w/v), preferably at a concentration ranging between 0.2% (w/v) and 1.5% (w/v).

In other embodiments, the aqueous compositions according to the invention comprise albumin (preferably any of the preferred albumins mentioned herein) at a concentration ranging between 0.5% (w/v) and 2% (w/v), preferably at a concentration ranging between 0.5% (w/v) and 1.5% (w/v).

In other embodiments, the aqueous compositions according to the invention comprise albumin (preferably any of the preferred albumins mentioned herein) at a concentration ranging between 0.8% (w/v) and 1.2% (w/v).

In other embodiments, the aqueous compositions according to the invention comprise albumin (preferably any of the preferred albumins mentioned herein) at a concentration of 0.1% (w/v), 0.25 (w/v). 0.5% (w/v), or 1% (w/v).

In one embodiment, the aqueous composition comprises Tris buffer, sodium chloride, sucrose, sorbitol, and arginine, but no added serum albumin.

Buffer and pH

The aqueous compositions according to any of the embodiments of the invention preferably have a pH ranging between pH 7.0 and pH 8.5.

In other embodiment of the invention, the aqueous compositions according to any of the embodiments have a pH ranging between pH 7.3 and pH 8.1.

In other embodiment of the invention, the aqueous compositions according to any of the embodiments have a pH of 7.7.

The skilled person familiar with pharmaceutical development is well aware of buffers which can be used to achieve a pH between e.g., pH 7.0 and pH 8.5. Such buffers preferably are selected from the group of phosphate buffer, Tris (Tris(hydroxymethyl)aminomethane), Tris-HCl (Tris (hydroxymethyl)aminomethane-HCl), Tricine (N-[tris(hydroxymethyl)methyl)-methyl]-glycine), and HEPES (4-2-hydroxyethyl-1-piperazineethansulfonic acid). The phosphate buffer preferably comprises a mixture of $Na_2HPO_4$ and $KH_2PO_4$ or a mixture of $Na_2HPO_4$ and $NaH_2PO_4$. In certain embodiments, the buffer of the aqueous composition is a Tris buffer, preferably a Tris-HCl buffer.

In certain embodiments the aqueous compositions according to any of the embodiments does not comprise citrate or citrate buffer.

In certain embodiments, the buffer of the aqueous compositions according to any of the embodiments is preferably present at a concentration ranging between 1 mM and 50 mM, preferably ranging between 1 mM and 25 mM.

In certain embodiments, the buffer of the aqueous compositions according to any of the embodiments is present at a concentration ranging between 1 mM and 15 mM, preferably ranging between 5 mM and 11 mM, more preferably ranging between 7 mM and 10 mM.

In certain embodiments, the buffer of the aqueous compositions according to any of the embodiments is present at a concentration of 10 mM.

In certain embodiments, the buffer of the aqueous compositions according to any of the embodiments is present at a concentration of 7.5 mM.

In a preferred embodiment, the buffer is 10 mM Tris-HCl buffer.

Salts

In other embodiments, the aqueous compositions according to any of the embodiments comprise a monovalent salt. Said monovalent salt is preferably sodium chloride (NaCl) or potassium chloride (KCl), preferably NaCl. Said NaCl is preferably present at a concentration of between 40 mM and 200 mM, preferably between 40 mM and 150 mM.

In another embodiment, NaCl may be present at a concentration of between 40 mM and 140 mM, 40 mM and 130 mM, 40 mM and 120 mM, 40 mM and 110 mM, 40 mM and 100 mM, 40 mM and 90 mM, 40 mM and 80 mM, 50 mM and 150 mM, 50 mM and 140 mM, 50 mM and 130 mM, 50 mM and 120 mM, 50 mM and 110 mM, 50 mM and 100 mM, 50 mM and 90 mM, 50 mM and 80 mM, 60 mM and 150 mM, 60 mM and 140 mM, 60 mM and 130 mM, 60 mM and 120 mM, 60 mM and 110 mM, 60 mM and 100 mM, 60 mM and 90 mM, 60 mM and 80 mM, 70 mM and 150 mM, 70 mM and 140 mM, 70 mM and 130 mM, 70 mM and 120 mM, 70 mM and 110 mM, 70 mM and 100 mM, 70 mM and 90 mM, or 70 mM and 80 mM.

In another embodiment, NaCl may be present at a concentration of between 60 mM and 80 mM.

In another embodiment, NaCl may be present at a concentration of between 70 mM.

In other embodiments, the aqueous compositions according to any of the embodiments comprise a divalent salt. Said divalent salt is preferably magnesium chloride ($MgCl_2$). Said $MgCl_2$ is preferably present at a concentration of between 1 mM and 300 mM.

In another embodiment, $MgCl_2$ may be present at a concentration of between 2 mM and 300 mM, 5 mM and 300 mM, 10 mM and 300 mM, 20 mM and 300 mM, 30 mM and 300 mM, 40 mM and 300 mM, 50 mM and 300 mM, 60 mM and 300 mM, 70 mM and 300 mM, 80 mM and 300 mM, 90 mM and 300 mM, 100 mM and 300 mM, 150 mM and 300 mM, 180 mM and 300 mM, 200 mM and 300 mM, 2 mM and 260 mM, 5 mM and 260 mM, 10 mM and 260 mM, 20 mM and 260 mM, 30 mM and 260 mM, 40 mM and 260 mM, 50 mM and 260 mM, 60 mM and 260 mM, 70 mM and 260 mM, 80 mM and 260 mM, 90 mM and 260 mM, 100 mM and 260 mM, 150 mM and 260 mM, 180 mM and 260 mM, 200 mM and 260 mM, 75 mM and 300 mM, 75 mM and 260 mM, 100 mM and 260 mM, 120 mM and 260 mM, 150 mM and 260 mM, 200 mM and 260 mM, 2 mM and 200 mM, 5 mM and 200 mM, 10 mM and 200 mM, 20 mM and 200 mM, 30 mM and 200 mM, 40 mM and 200 mM, 50 mM and 200 mM, 60 mM and 200 mM, 70 mM and 200 mM, 80 mM and 200 mM, 90 mM and 200 mM, 2 mM and 150 mM, 5 mM and 150 mM, 10 mM and 150 mM, 20 mM and 150 mM, 30 mM and 150 mM, 40 mM and 150 mM, 50 mM and 150 mM, 60 mM and 150 mM, 70 mM and 150 mM, 80 mM and 150 mM, 90 mM and 150 mM, 2 mM and 100 mM, 5 mM and 100 mM, 10 mM and 100 mM, 20 mM and 100 mM, 30 mM and 100 mM, 40 mM and 100 mM, 50 mM and 100 mM, 60 mM and 100 mM, 70 mM and 100 mM, 80 mM and 100 mM, 90 mM and 100 mM, 2 mM and 75 mM, 5 mM and 75 mM, 10 mM and 75 mM, 20 mM and 75 mM, 30 mM and 75 mM, 40 mM and 75 mM, 50 mM and 75 mM, 60 mM and 75 mM, 70 mM and 75 mM, 2 mM and 50 mM, 5 mM and 50 mM, 10 mM and 50 mM, 20 mM and 50 mM, 30 mM and 50 mM, 40 mM and 50 mM, 2 mM and 40 mM, 5 mM and 40 mM, 10 mM and 40 mM, 20 mM and 40 mM, or 30 mM and 40 mM.

In another embodiment, $MgCl_2$ may be present at a concentration of between 75 mM and 300 mM.

In another embodiment, $MgCl_2$ may be present at a concentration of between 100 mM and 300 mM.

In another embodiment, $MgCl_2$ may be present at a concentration of between 200 mM and 300 mM.

In another embodiment, $MgCl_2$ may be present at a concentration of between 220 mM and 260 mM.

In another embodiment, $MgCl_2$ may be present at a concentration of between 240 mM and 260 mM.

In other embodiments, the aqueous compositions according to any of the embodiments comprise a monovalent salt and a divalent salt, preferably in any concentration as indicated above.

In another embodiment, the aqueous compositions according to any of the embodiments comprise a monovalent salt at a concentration of between 60 mM and 80 mM and a divalent salt at a concentration of between 220 and 260 mM.

In another embodiment, the aqueous compositions according to any of the embodiments comprise NaCl at a concentration of between 40 mM and 150 mM and $MgCl_2$ at a concentration of between 220 mM and 260 mM.

In another embodiment, the aqueous compositions according to any of the embodiments comprise NaCl at a concentration of between 70 mM and 150 mM and $MgCl_2$ at a concentration of between 220 mM and 260 mM.

In another embodiment, the aqueous compositions according to any of the embodiments comprise NaCl at a concentration of between 60 mM and 80 mM and $MgCl_2$ at a concentration of between 220 mM and 260 mM.

In another embodiment, the aqueous composition is free of $MgCl_2$ and/or $CaCl_2$.

In a preferred embodiment, the aqueous composition comprises 140 mM NaCl.

Amino Acids

The aqueous compositions according to any of the embodiments described herein may contain one or more amino acid(s). Preferred amino acids are histidine, arginine, lysine glycine and/or glutamic acid or salts thereof, in particular the L-isomer L-histidine, L-arginine, L-lysine, L-glycine and/or L-glutamic acid or salts thereof. Said amino acid(s) is/are not an amino acid encoded by the recombinant or non-recombinant virus of the present invention. Thus, the amino acid is not contained in the composition through the process of purification of the virus (e.g., MVA) but added during the generation of the composition for manufacturing a vaccine. Mostly preferred is L-arginine, e.g. L-arginine HCl.

The amino acid is preferably present at a concentration below 150 mM, below 130 mM, below 120 mM, preferably below 110 mM.

In further embodiments, the amino acid is present at a concentration ranging between 10 mM and 110 mM, 20 mM and 110 mM, 30 mM and 110 mM, 40 mM and 110 mM, 50 mM and 110 mM, 60 mM and 110 mM, 70 mM and 110 mM, or 80 mM and 110 mM.

In further embodiments, the amino acid is present at a concentration ranging between 40 mM and 110 mM.

In further embodiments, the amino acid is present at a concentration ranging between 90 mM and 110 mM.

In further embodiments, the amino acid is present at a concentration of 100 mM.

In further embodiments, the amino acid is present at a concentration of 50 mM.

In further embodiments, the aqueous composition of the invention may contain histidine (preferably L-histidine) at a concentration of between 40 mM and 60 mM.

In further embodiments, the aqueous composition of the invention may contain arginine (preferably L-arginine) at a concentration of between 40 mM and 60 mM.

In further embodiments, the aqueous composition of the invention may contain lysine (preferably L-lysine) at a concentration of between 40 mM and 60 mM.

In further embodiments, the aqueous composition of the invention may contain glycine (preferably L-glycine) at a concentration of between 40 mM and 60 mM.

In further embodiments, the aqueous composition of the invention may contain histidine, arginine, lysine and glycine, preferably each at a concentration of between 40 mM and 60 mM.

In further embodiments, the aqueous composition of the invention may contain histidine, arginine, lysine and glycine, preferably each at a concentration of between 40 mM and 60 mM.

The concentrations of the amino acid described above may be used for any of the specific amino acids mentioned in the section above (e.g., histidine, arginine, lysine and/or glycine).

Glutamic acid or salts thereof (e.g., monosodium glutamate or monosodium glutamate monohydrate) are preferably present at a concentration of between 2.5 mM and 7.5 mM.

In further embodiments, glutamic acid or salts thereof (e.g., monosodium glutamate monohydrate or monosodium glutamate monohydrate) are present at a concentration ranging between 3 mM and 6 mM. Preferably, glutamic acid or salts thereof (e.g., monosodium glutamate monohydrate or monosodium glutamate monohydrate)) are present at a concentration of 5 mM.

In a preferred embodiment, the aqueous composition of the invention is substantially free or is free of glutamic acid. Preferably, the aqueous composition is substantially free or is free of an added amino acid except for arginine.

In a preferred embodiment, the aqueous composition of the invention comprises Tris buffer, sodium chloride, sucrose, sorbitol, and arginine, but no other added amino acid.

Further Excipients

The aqueous compositions according to any of the embodiments described herein may further comprise octanoate. Preferably the aqueous compositions according to any of the embodiments comprises octanoate ion at a concentration of less than or equal to 5 mM, preferably of less or equal than 1 mM, more preferably 0.001 to 1 mM.

The aqueous compositions according to any of the embodiments described herein may further comprise one or more additional carrier, additive, antibiotic, preservative, adjuvant, and/or diluent, preferably, any of the additional carrier, additive, antibiotic, preservative, adjuvant, and/or diluent is pharmaceutically acceptable.

In further embodiments, the aqueous composition of the present invention is free of mannitol.

In further embodiments, the aqueous composition of the present invention is substantially free of citrate.

In further embodiments, the aqueous composition of the present invention is free of citrate.

In further embodiments, the aqueous composition of the present invention is substantially pharmaceutically acceptable or is pharmaceutically acceptable.

In other embodiments, the aqueous composition of the present invention is a vaccine or pharmaceutical composition.

In further embodiments, the aqueous composition of the present invention is substantially free of mannitol.

In further embodiments, the aqueous composition is substantially free of a chelating agent. Examples of chelating agents include ethylenediaminetetraacetic acid (EDTA), 1,2-bis(o-aminophenoxy)ethane-N,N,N',N'-tetraacetic acid (BAPTA), ethylene glycol tetraacetic acid (EGTA), dimercaptosuccinic acid (DMSA), diethylene triamine pentaacetic acid (DTPA), and 2,3-Dimercapto-1-propanesulfonic acid (DMPS). "Substantially free of a chelating agent" according to the present invention means less than 50 µM of the chelating agent.

In further embodiments, the aqueous composition of the present invention is free of a chelating agent.

In further embodiments, the aqueous composition of the present invention is substantially free of polysorbate. Examples of polysorbate include polysorbate 80.

In further embodiments, the aqueous composition of the present invention is free of polysorbate.

In further embodiments, the aqueous composition of the present invention is substantially free of a $C_2$-$C_3$ alcohol, wherein the $C_2$-$C_3$ alcohol is ethanol and/or isopropanol. "Substantially free of a $C_2$-$C_3$ alcohol" according to the present invention means less than 0.05 (v/v) of ethanol or isopropanol.

In further embodiments, the aqueous composition of the present invention is free of a $C_2$-$C_3$ alcohol, wherein the $C_2$-$C_3$ alcohol is ethanol and/or isopropanol.

In further embodiments, the aqueous composition of the present invention is substantially free of mannitol, citrate, a chelating agent, $C_2$-$C_3$ alcohol (i.e., ethanol and/or isopropanol) and/or polysorbate.

In further embodiments, the aqueous composition of the present invention is free of mannitol, citrate, a chelating agent, $C_2$-$C_3$ alcohol (i.e., ethanol and/or isopropanol) and/or polysorbate.

In further embodiments, the aqueous composition of the present invention is substantially free of HPBCD and mannitol.

In further embodiments, the aqueous composition of the present invention is free of HPBCD and mannitol.

In further embodiments, the aqueous composition of the present invention is substantially free of HPBCD, mannitol and citrate.

In further embodiments, the aqueous composition of the present invention is free of HPBCD, mannitol and citrate.

In further embodiments, the aqueous composition of the present invention is substantially free of HPBCD, mannitol, citrate, a chelating agent, and $C_2$-$C_3$ alcohol (i.e., ethanol and/or isopropanol).

In further embodiments, the aqueous composition of the present invention is free of HPBCD, mannitol, citrate, a chelating agent, and $C_2$-$C_3$ alcohol (i.e., ethanol and/or isopropanol).

In further embodiments, the aqueous composition of the present invention is substantially free of HPBCD, mannitol, citrate, a chelating agent, $C_2$-$C_3$ alcohol (i.e., ethanol and/or isopropanol) and polysorbate.

In further embodiments, the aqueous composition of the present invention is free of HPBCD, mannitol, citrate, a chelating agent, $C_2$-$C_3$ alcohol (i.e., ethanol and/or isopropanol) and polysorbate.

In further embodiments, the aqueous composition of the present invention is substantially free or is free of serum albumin. Particularly, an aqueous composition comprising arginine may be free of serum albumin.

In further embodiments, the aqueous composition of the present invention is substantially free or is free of gelatin. Particularly, an aqueous composition comprising arginine may be free of gelatin.

In further embodiments, the aqueous composition of the present invention is substantially free or is free of arginine. Particularly, an aqueous composition comprising serum albumin and/or gelatin may be free of arginine.

Miscellaneous

In other embodiments the aqueous composition according to the present invention is contained in a vial. The term "vial" refers to any container, vessel, cartridge, device, glass ampoule, or syringe capable for storage of active pharmaceutical ingredients such as the viruses as disclosed herein. The terms vial, container, vessel, cartridge, device, glass ampoule, or syringe can thus be used interchangeably. The vial is usually made of inert material, in particular glass (such as DIN 2R type I borosilicate glass viral) or polymeric material. In a preferred embodiment the composition is contained in DIN 2R type I borosilicate glass viral. In a preferred embodiment the composition is contained in a syringe.

The composition of the present invention can be administered to the subject preferably a human by any means known in the art. The routes of administration include but are not limited to intramuscular injection, subcutaneous injection, intradermal injection, intravenous application, intranasal administration, transdermal administration, transcutaneous administration, or percutaneous administration. The mode of administration, the dose and the number of administrations can be optimized by those skilled in the art in a known manner. In a preferred embodiment, the aqueous composition of the present invention is suitable for parenteral administration or application. In other preferred embodiments, the aqueous composition of the present invention is suitable for intranasal administration or application. In other preferred embodiments, the aqueous composition of the present invention is suitable for intramuscular or subcutaneous administration or application.

In certain embodiments, the aqueous composition of any of the embodiments of the present invention is further defined as having an infectivity of at least 50%, 60%, 79%, 80% or 90% of the starting infectivity (at day 0) when stored for three months at +5 degrees C.

In certain embodiments, the aqueous composition of any of the embodiments of the present invention is further defined as having an infectivity of at least 70%, 80% or 90% of the starting infectivity (at day 0) when stored for three months at −20 degrees C.

In certain embodiments, the aqueous composition of any of the embodiments of the present invention is further defined as having an infectivity of at least 70%, 80% or 90% of the starting infectivity (at day 0) when stored for six months at +5 degrees C.

In certain embodiments, the aqueous composition of any of the embodiments of the present invention is further defined as having an infectivity of at least 70%, 80% or 90% of the starting infectivity (at day 0) when stored for six months at −20 degrees C.

In certain embodiments, the aqueous composition of any of the embodiments of the present invention is further defined as having an infectivity of at least 70%, 80% or 90% of the starting infectivity (at day 0) when stored for five months at +25 degrees C./60% relative humidity.

According to particular embodiments, the aqueous composition of the present invention is stable.

According to particular embodiments, the aqueous composition of the present invention is stable when the overall loss of virus titer at +5 degrees C. for at least 3 months is less than 0.5 $\log_{10}$ InfU/mL, preferably less than 0.4 $\log_{10}$ InfU/mL, more preferably less than 0.3 $\log_{10}$ InfU/mL, most preferably less than 0.2 $\log_{10}$ InfU/mL, preferably as determined by a Fluorescence Activated Cell Sorter (FACS) assay.

According to particular embodiments, the aqueous composition of the present invention is stable when the overall loss of virus titer at +5 degrees C. for at least 6 months is less than 0.5 $\log_{10}$ InfU/mL, preferably less than 0.4 $\log_{10}$ InfU/mL, more preferably less than 0.3 $\log_{10}$ InfU/mL, most preferably less than 0.2 $\log_{10}$ InfU/mL, preferably as determined by a Fluorescence Activated Cell Sorter (FACS) assay.

According to particular embodiments, the aqueous composition of the present invention is stable when the overall loss of virus titer at +5 degrees C. for at least 9 months is less than 0.5 $\log_{10}$ InfU/mL, preferably less than 0.4 $\log_{10}$ InfU/mL, more preferably less than 0.3 $\log_{10}$ InfU/mL, most preferably less than 0.2 $\log_{10}$ InfU/mL, preferably as determined by a Fluorescence Activated Cell Sorter (FACS) assay.

According to particular embodiments, the aqueous composition of the present invention is stable when the overall loss of virus titer at +5 degrees C. for at least 12 months is less than 0.5 $\log_{10}$ InfU/mL, preferably less than 0.4 $\log_{10}$ InfU/mL, more preferably less than 0.3 $\log_{10}$ InfU/mL, most preferably less than 0.2 $\log_{10}$ InfU/mL, preferably as determined by a Fluorescence Activated Cell Sorter (FACS) assay.

According to particular embodiments, the aqueous composition of the present invention is stable when the overall loss of virus titer at −20 degrees C. for at least 3 months is less than $0.5 \log_{10}$ InfU/mL, preferably less than $0.4 \log_{10}$ InfU/mL, more preferably less than $0.3 \log_{10}$ InfU/mL, most preferably less than $0.2 \log_{10}$ InfU/mL, preferably as determined by a Fluorescence Activated Cell Sorter (FACS) assay.

According to particular embodiments, the aqueous composition of the present invention is stable when the overall loss of virus titer at −20 degrees C. for at least 6 months is less than $0.5 \log_{10}$ InfU/mL, preferably less than $0.4 \log_{10}$ InfU/mL, more preferably less than $0.3 \log_{10}$ InfU/mL, most preferably less than $0.2 \log_{10}$ InfU/mL, preferably as determined by a Fluorescence Activated Cell Sorter (FACS) assay.

According to particular embodiments, the aqueous composition of the present invention is stable when the overall loss of virus titer at −20 degrees C. for at least 9 months is less than $0.5 \log_{10}$ InfU/mL, preferably less than $0.4 \log_{10}$ InfU/mL, more preferably less than $0.3 \log_{10}$ InfU/mL, most preferably less than $0.2 \log_{10}$ InfU/mL, preferably as determined by a Fluorescence Activated Cell Sorter (FACS) assay.

According to particular embodiments, the aqueous composition of the present invention is stable when the overall loss of virus titer at −20 degrees C. for at least 12 months is less than $0.5 \log_{10}$ InfU/mL, preferably less than $0.4 \log_{10}$ InfU/mL, more preferably less than $0.3 \log_{10}$ InfU/mL, most preferably less than $0.2 \log_{10}$ InfU/mL, preferably as determined by a Fluorescence Activated Cell Sorter (FACS) assay According to particular embodiments, the aqueous composition of the present invention is stable when the overall loss of virus titer at +25 C/60% relative humidity for at least 5 months is less than $0.5 \log_{10}$ InfU/mL, preferably less than $0.4 \log_{10}$ InfU/mL, more preferably less than $0.3 \log_{10}$ InfU/mL, most preferably less than $0.2 \log_{10}$ InfU/mL, preferably as determined by a Fluorescence Activated Cell Sorter (FACS) assay.

According to particular embodiments, the aqueous composition of the present invention is stable for a time period of at least 12 months at about −20 degrees C. followed storage at +2 to +8 degrees C. for 3 months, wherein the overall loss of virus titer at −20 degrees C. for the specified time period of at least 12 months followed by storage at +2 to +8 degrees C. for at least 3 months is less than $0.5 \log_{10}$ InfU/mL. Preferably the overall loss of virus titer is less than $0.4 \log_{10}$ InfU/mL, more preferably less than $0.3 \log_{10}$ InfU/mL, most preferably less than $0.2 \log_{10}$ InfU/mL, preferably as determined by a Fluorescence Activated Cell Sorter (FACS) assay by determined by a Fluorescence Activated Cell Sorter (FACS) assay.

According to particular embodiments, the aqueous composition of the present invention is stable for a time period of at least 12 months at about −20 degrees C. followed by storage at +2 to +8 degrees C. for 9 months, wherein the overall loss of virus titer at −20 degrees C. for the specified time period of at least 12 months followed by storage at +2 to +8 degrees C. for at least 9 months is less than $0.5 \log_{10}$ InfU/mL. Preferably the overall loss of virus titer is less than $0.4 \log_{10}$ InfU/mL, more preferably less than $0.3 \log_{10}$ InfU/mL, most preferably less than $0.2 \log_{10}$ InfU/mL, preferably as determined by a Fluorescence Activated Cell Sorter (FACS) assay.

According to particular embodiments, the aqueous composition of the present invention is stable for a time period of at least 24 months at about −20 degrees C. followed by storage at +2 to +8 degrees C. for 9 months, wherein the overall loss of virus titer at −20 degrees C. for the specified time period of at least 24 months followed by storage at +2 to +8 degrees C. for at least 9 months is less than $0.5 \log_{10}$ InfU/mL. Preferably the overall loss of virus titer is less than $0.4 \log_{10}$ InfU/mL, more preferably less than $0.3 \log_{10}$ InfU/mL, most preferably less than $0.2 \log_{10}$ InfU/mL, preferably as determined by a Fluorescence Activated Cell Sorter (FACS) assay.

The "overall loss of virus titer" according to the present invention is defined as the cumulative loss in virus titer measured during storage of the composition at the indicated temperature n (e.g., at +5 degrees C.) and time t (e.g., for 6 months) given as $\log_{10}$ InfU/mL. The overall loss of virus titer is given as x $\log_{10}$ (e.g., as $0.5 \log_{10}$ at +5 degrees C. for six months).

According to particular embodiments, the aqueous composition of the present invention is stable, wherein the composition exhibits a potency loss of less than $0.3 \log_{10}$ InfU/mL when stored for a period of 12 months at −20 degrees C.

According to particular embodiments, the aqueous composition of the present invention is stable, wherein the composition exhibits a potency loss of less than $0.3 \log_{10}$ InfU/mL when stored for a period of 12 months at +4 degrees C. to +8 degrees C.

According to particular embodiments, the aqueous composition of the present invention is stable, wherein the composition exhibits a potency loss of less than $0.2 \log_{10}$ InfU/mL when stored for a period of 12 months at −20 degrees C.

According to particular embodiments, the aqueous composition of the present invention is stable, wherein the composition exhibits a potency loss of less than $0.2 \log_{10}$ InfU/mL when stored for a period of 12 months at +4 degrees C. to +8 degrees C.

According to particular embodiments, the aqueous composition of the present invention is stable, wherein the composition exhibits a potency loss of less than $0.1 \log_{10}$ InfU/mL when stored for a period of 12 months at −20 degrees C.

According to particular embodiments, the aqueous composition of the present invention is stable, wherein the composition exhibits a potency loss of less than $0.1 \log_{10}$ InfU/mL when stored for a period of 12 months at +4 degrees C. to +8 degrees C.

According to particular other embodiments, the aqueous composition of the present invention is a liquid composition or a liquid frozen composition.

According to particular other embodiments, the aqueous composition of the present invention is an aqueous frozen composition.

According to particular other embodiments, the aqueous composition of the present invention is an aqueous liquid composition.

According to particular other embodiments, the aqueous composition of the present invention is not a dried composition, preferably not a freeze-dried or lyophilized composition.

Another aspect provides the aqueous composition of the present invention for treating or preventing a disease, preferably an infectious disease or cancer.

Another aspect provides a use of the aqueous composition of the present invention for manufacturing a medicament or vaccine for treating or preventing an infectious disease or cancer.

Another aspect provides a method of treating or preventing an infectious disease, administering to the subject the composition of any of the embodiments of the invention.

Definitions and Terminology

It is to be understood that both the foregoing summary and the detailed description are exemplary and explanatory only and are not restrictive of the invention, as claimed. It is to be understood that this invention is not limited to a particular methodology, protocols and reagents described herein as these may vary. It is also to be understood that the terminology used herein is for the purpose of describing particular embodiments only and is not intended to limit the scope of the present invention which will be limited only by the appended claims. Unless defined otherwise, all technical and scientific terms used herein have the same meanings as commonly understood by one of ordinary skill in the art.

Terms are defined and explained so that the invention may be understood more readily. Additional definitions are set forth throughout the detailed description.

It must be noted that, as used herein, the singular forms "a", "an", and "the", include plural references unless the context clearly indicates otherwise. Thus, for example, reference to "a nucleic acid" includes one or more nucleic acid sequences and reference to "the method" includes reference to equivalent steps and methods known to those of ordinary skill in the art that could be modified or substituted for the methods described herein.

Unless otherwise indicated, the term "at least" preceding a series of elements is to be understood to refer to every element in the series. Those skilled in the art will recognize or be able to ascertain using no more than routine experimentation, many equivalents to the specific embodiments of the invention described herein. Such equivalents are intended to be encompassed by the present invention.

As used herein, the conjunctive term "and/or" between multiple recited elements is understood as encompassing both individual and combined options. For instance, where two elements are conjoined by "and/or", a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used in the context of an aspect or embodiment in the description of the present invention the term "comprising" can be amended and thus replaced with the term "containing" or "including" or when used herein with the term "having." Similarly, any of the aforementioned terms (comprising, containing, including, having), whenever used in the context of an aspect or embodiment in the description of the present invention include, by virtue, the terms "consisting of" or "consisting essentially of," which each denotes specific legal meaning depending on jurisdiction.

When used herein "consisting of" excludes any element, step, or ingredient not specified in the claim element. When used herein, "consisting essentially of" does not exclude materials or steps that do not materially affect the basic and novel characteristics of the claim.

The term "substantially free of" an ingredient as used herein does not exclude trace amounts of the ingredient which does not materially affect the stability of the composition of the present if not stated otherwise herein. The term "free of" in front of for example mannitol means that the aqueous composition of the present invention does not contain mannitol.

"About" as used in the present application means ±10%, unless stated otherwise. It must also be noted that unless otherwise stated, any numerical value, such as a concentration or a concentration range described herein, are to be understood as being modified in all instances by the term "about." Through the specification the term "about" with respect to any quantity or concentration is contemplated to include that quantity. For example, "about 5 mM" is contemplated herein to include 5 mM as well as values understood to be approximately 5 mM with respect to the entity described. As used herein, the use of a numerical range expressly includes all possible subranges, all individual numerical values within that range, including integers within such ranges and fractions of the values unless the context clearly indicates otherwise. Likewise, the term "about" preceding any numerical value or range used herein in the context of the invention can be deleted and be replaced by the numerical value or range without the term "about" though less preferred.

The term "nucleic acid", "nucleotide sequence", "nucleic acid sequence" and "polynucleotide" can be used interchangeably and refers to RNA or DNA that is linear or branched, single or double stranded, or a hybrid thereof. The polynucleotides can be obtained by chemical synthesis or derived from a microorganism. The term "exogenous" nucleic acid sequences when used in connection with a recombinant virus means a foreign nucleic acid sequence, a nucleic acid sequence not contained in the non-recombinant virus used for generating the recombinant virus or inserted into the virus genome while generating the recombinant virus.

"Pharmaceutically acceptable" means that the carrier, additive, antibiotic, preservative, adjuvant, diluent, stabilizer or excipient, at the dosages and concentrations employed, will substantially not cause an unwanted or harmful effect(s) in the subject(s) to which they are administered. A "pharmaceutically acceptable" excipient is any inert substance that is combined with an active molecule such as a virus for preparing an agreeable or convenient dosage form. The "pharmaceutically acceptable" excipient is non-toxic to recipients at the dosages and concentrations employed and is compatible with other ingredients of the formulation comprising the viral preparation. Examples of excipients are cryoprotectants, non-ionic detergents, buffers, salts and inhibitors of free radical oxidation. "Pharmaceutically acceptable carriers" are for example described in Remington's Pharmaceutical Sciences, 18th edition, A. R. Gennaro, Ed., Mack Publishing Company (1990); Pharmaceutical Formulation Development of Peptides and Proteins, S. Frokjaer and L. Hovgaard, eds., Taylor & Francis [2000]; and Handbook of Pharmaceutical Excipients, 3rd edition, A. Kibbe, Ed., Pharmaceutical Press (2000).

By "stable", "stabilized", "stability" or "stabilizing", which can all be used interchangeable, it is understood that the poxvirus contained in the composition of the present invention essentially retains its physical stability, identity, integrity, and/or chemical stability, identity, integrity, particle morphology and/or biological activity or potency upon storage required for shelf-life of a pharmaceutical composition. As used herein, the term "shelf-life" means the time that a product remains active and/or stable according to the product characteristics under specified storage conditions (e.g., storage at +2 degrees C. to +8 degrees C.) for use as a human medication. Shelf-lives correspond to the time points for which the lower limit or upper limit of a given specification is exceeded.

Stability can be assessed by determining different characteristics such as the quantity (of poxviruses in a formulation), the potency, and/or other quality aspects of the poxvirus (e.g., MVA) in the formulation over a period of time and under certain storage conditions. These characteristics of a poxvirus (e.g., MVA) formulation can be measured at elevated temperatures (predictive for real-time temperatures) or under other stress conditions, for instance formulations can be subjected to +20 degrees C. incubation, at +25 degrees C., at −20 degrees C. or +5 degrees C. or subjected to freeze/thaw cycles and agitation in order to study effects of different formulations maximizing shelf-life. Methods to determine stability of the poxvirus (e.g., MVA) are well known to the skilled person and may be determined by at least one method selected from the group of visual inspection, pH measurement, turbidity assay, particle morphology and potency (infectivity) assay.

Turbidimetry measures the loss of intensity of transmitted light due to scattering of particles in samples (apparent absorbance), detected at a wavelength where the molecules in the sample do not absorb light (e.g., 350 nm for samples in which proteins are the main chromophore). When molecules aggregate or form supramolecular complexes, the light scattering, which was random when coming from the separate particles, now becomes coherent, and thereby the measured intensity increases. This makes light scattering and turbidimetry useful techniques for detecting aggregation and complex formation or dissociation.

In the turbidity assay, samples are transferred in triplicate to a UV-transparent, flat-bottom microplate. Absorbance spectra are recorded by a microplate reader between 230 and 500 nm, and the absorbance at 975 nm is measured to determine and possibly correct for differences in optical path length. Control samples consisting of the formulations without MVA were included in the assay to correct for scattering or absorbing matrix components if required. The apparent absorbance at 350 nm was used as a quantitative measure for turbidity.

The turbidity assay is stability-indicating for MVA samples. MVA aggregation leads to an increase in turbidity and capsid dissociation to a decrease. The assay precision is <5% (CV %) at turbidity values>1 NTU.

Methods to determine particle morphology are well known to the skilled person. For example, particle morphology can be determined using transmission electron microscopy and immunoelectron microscopy (immune-EM) as for example described in Schweneker et al. *J Virol* 2017, 91: e00343-00317. Alternative methods to determine particle morphology is the Nanoparticle Tracking Analysis (NTA) described for example in Filipe et al. *Pharm Res* 2010, 27: 796-810. Nanoparticle tracking analysis (NTA) is a method for the direct and real-time visualization and analysis of particle size distribution and aggregation in liquids. Based on a laser illuminated microscopic technique, Brownian motion of nanoparticles is analyzed in real-time by a charge-couple device (CCD) camera, each particle being simultaneously but separately visualized and tracked by a dedicated particle tracking image-analysis program. The ability of NTA to measure simultaneously particle size and particle scattering intensity allows heterogeneous particle mixtures to be resolved and particle concentration to be estimated directly.

The term "potency" or "infectivity", when used in relation to a virus as used herein refers to the ability of the virus to infect cells, referring to the invasion and multiplication of the virus in a cell or organism. Infectivity thus refers to the activity of the poxvirus (e.g., vaccinia virus or MVA) expressed as infectious units (InfU) usually given as InfU/mL. Both terms "potency" and "infectivity" can be used interchangeably in the present invention. The potency of a poxvirus such as MVA can be determined using various methods known to the skilled person such as for example determining the percentage of virus-positive cells such as Baby Hamster Kidney Cells 21 (BHK-21) after infection with the virus. A preferred assay is for example the Fluorescence Activated Cell Sorter (FACS) assay as described in the examples.

The terms "subject" and "patient" are used interchangeably. As used herein, a subject is typically a mammal, such as a non-primate (e.g., cows, pigs, horses, cats, dogs, rats, etc.) or a primate (e.g., monkey and human), and in some preferred embodiments a human.

According to the present invention, "virus" means viruses, virus particles and viral vectors. The terms can all be used interchangeably. This term includes wild-type viruses, recombinant and non-recombinant viruses, live viruses and live-attenuated viruses.

According to the present invention, a concentration given in % (w/v) means weight in gram (g) per volume in 100 mL for example 20% (w/v) means 20 g/100 mL. A concentration given in % (v/v) means weight in mL per volume in 100 mL for example 20% (v/v) means 20 mL/100 mL.

Throughout the specification, except where stated otherwise, values of physical parameters such as pH are those measured at +25 degrees C. or around +25 degrees C. Particularly, pH measurements may be carried out at ambient temperature.

Several documents are cited throughout the text of this specification. Each of the documents cited herein (including all patents, patent applications, scientific publications, manufacturer's specifications, instructions, etc.), whether supra or infra, are hereby incorporated by reference in their entirety. To the extent, the material incorporated by reference contradicts or is inconsistent with this specification, the specification will supersede any such material. Nothing herein is to be construed as an admission that the invention is not entitled to antedate such disclosure by virtue of prior invention.

The practice of the invention will employ, if not otherwise specified, conventional techniques of immunology, molecular biology, microbiology, cell biology, and recombinant technology, which are all within the skill of the art. See e.g. Sambrook, Fritsch and Maniatis, Molecular Cloning: A Laboratory Manual, 2nd edition, 1989; Current Protocols in Molecular Biology, Ausubel F M, et al., eds, 1987; the series Methods in Enzymology (Academic Press, Inc.); PCR2: A Practical Approach, MacPherson M J, Hams B D, Taylor G R, eds, 1995; Antibodies: A Laboratory Manual, Harlow and Lane, eds, 1988.

EXAMPLES

The following examples illustrate the invention but should not be construed as in any way limiting the scope of the claims. They merely serve to clarify the invention.

Example 1: Generation of Recombinant MVA

Recombinant MVA used for the stability studies was MVA-BN-RSV (MVA-mBN294B) as described in WO 2015/136056 incorporated by reference herewith. MVA-mBN294B encodes for an RSV-F(Along) protein, a G(A) and G(B) protein, as well as an N and M2-1 protein, wherein the N and M2-1 sequences are encoded by a single open reading frame separated by a 2A self-cleavage protease domain of the FMDV virus. As integration site for the antigens IGR 64/65 and IGR 148/149 were used. The genes were expressed under the poxvirus promoters Pr7.5e/1 (Cochran et al. *J Virol* 1985, 54: 30-37), PrS (Chakrabarti et al. *Biotechniques* 1997, 23: 1094-1097), PrLE1 (Baur et al. *J Virol* 2010, 84: 8743-8752) and PrH5m (Wenner et al. *PLoS One* 2013, 8: e73511) as described in WO 2015/136056.

MVA-BN-RSV (MVA-mBN294B) was produced in chicken embryonic fibroblast (CEF) cells. CEF cells were produced using standard methods well known to the skilled person such as described in WO 2012/010280. Several methods are available to amplify the recombinant MVA virus and to purify bulk drug substance (BDS) which are also well known to the skilled person (e.g. as described in WO 2006/052826).

MVA-BN-RSV (MVA-mBN294B) was produced in CEF cells using a bioreactor process. The cells were seeded into the bioreactor with additives (L-glutamine and poloxamer) and VP-SFM media. The cells were cultivated on micro carrier over a period of 6-7 days until desired density of cells was obtained for infection.

After the infection and the production of MVA-BN-RSV (MVA-mBN294B), cells were recovered by agitation and the micro carriers were removed of by sieving. Cells were recovered and homogenized by ultrasonification to lyse the cells and release virus particles produced. The purified virus was concentrated by centrifugation to finally obtain the purified bulk drug substance. The BDS was stored at −80 degrees C.±10 degrees C.

Example 2: Formulations of Recombinant MVA

The individual compositions of formulations F23 and F69 to F88 regarding recombinant human serum albumin (rHSA), gelatin and arginine are presented in Table 1 below. The numbers of formulations and thus the order in which they were prepared was randomized using a random sequence generator. All formulations contained MVA-BN-RSV (always from the same BDS batch) in an aqueous composition (pH 7.6-7.9) of 10 mM Tris buffer, 140 mM NaCl, 10% (w/v) sucrose, and 2% (w/v) sorbitol. The concentrations of rHSA, gelatin and arginine are indicated in Table 1.

TABLE 1-1

| Formulation | rHSA (%)* | Gelatin (%)* | Arginine (mM) |
|---|---|---|---|
| A: Formulations containing gelatin (3% or 1.5%) plus 0-1% rHSA. | | | |
| F23 | 1 | 3 | 0 |
| F77 | 0.5 | 3 | 0 |
| F69 | 0.25 | 3 | 0 |
| F85 | 0.1 | 3 | 0 |
| F80 | 1 | 1.5 | 0 |
| F76 | 0.5 | 1.5 | 0 |
| F75 | 0.25 | 1.5 | 0 |
| F87 | 0.1 | 1.5 | 0 |
| F81 | 0 | 1.5 | 0 |

TABLE 1-1-continued

| Formulation | rHSA (%)* | Gelatin (%)* | Arginine (mM) |
|---|---|---|---|
| B: Formulations containing 0-1% rHSA. | | | |
| F82 | 1 | 0 | 0 |
| F73 | 0.5 | 0 | 0 |
| F84 | 0.25 | 0 | 0 |
| F71 | 0.1 | 0 | 0 |
| F86 | 0 | 0 | 0 |
| C: Formulations containing arginine (100 mM) plus 0-1% rHSA. | | | |
| F78 | 1 | 0 | 100 |
| F83 | 0.5 | 0 | 100 |
| F74 | 0.25 | 0 | 100 |
| F88 | 0.1 | 0 | 100 |
| F72 | 0 | 0 | 100 |
| D: Formulation containing rHSA, gelatin and arginine. | | | |
| F70 | 0.5 | 3 | 100 |

*% = w/v

Preparation of the formulations: Concentrated BDS of MVA-BN-RSV as produced in Example 1 above was mixed into formulation buffer (10 mM Tris, 140 mM NaCl, 10% (w/v) sucrose, 2% (w/v) sorbitol) containing three-fold concentrations of rHSA, gelatin, arginine, and combinations, respectively (final one-fold concentrations as indicated in Table 1). The formulation buffers had been filtered using a 0.2 µm syringe before use. The formulated MVA-BN-RSV were filled into DIN 2-R glass vials (0.5 mL mL for FACS samples, 0.8 mL for pH samples).

The following raw materials were used for preparing the formulation buffers: Sorbitol EMPROVE® exp Ph Eur, BP, NF, JP Parteck® SI 400 LEX, Merck; Sucrose, EMPROVE® exp Ph Eur, BP, JP, NF, Low Endotoxin Merck; recombinant human albumin, Recombumin®, Albumedix; hydrolysed gelatin, Vaccipro®, Gelita; L-arginine, PharmaGrade, USP, Sigma Aldrich; sodium chloride BioXtra Sigma; Tris hydrochloride, VWR. MVA-mBN294B in 10 mM Tris and 140 mM sodium chloride at pH 7.7±0.4 was used as a control.

For each of the formulations, samples have been aliquoted for storage and analysis for various time points at +25 degrees C./60% RH (0, 3 weeks/19 day and 5 weeks/33 days) using triplicates. For each time point, vials were filled with 0.5 mL of the corresponding MVA-BN-RSV formulation and stored under the respective temperature for stability analysis thereafter. Vials used for pH measurement were filled with 0.8 mL.

At study start, vials containing the different formulations and corresponding to time zero (t=0) were transferred to −80 degrees Celsius, whereas the remaining vials were transferred to +25 degrees Celsius/60% RH (accelerated storage conditions), +5 degrees Celsius (real time) and −20 degrees Celsius (real time), respectively.

Example 3: Determination of Virus Titer

As a parameter of stability, the virus titer of MVA-BN-RSV was determined. A decrease in virus titer indicates an instability, which generally is to be expected during storage.

The titer (InfU/mL) of MVA-BN-RSV was determined by a potency (infectivity) assay using Fluorescence Activated Cell Sorting (FACS). MVA-BN-RSV infected Baby Hamster Kidney Cells 21 (BHK-21) cells were immune-stained with a fluorochrome-conjugated antibody specific for vaccinia virus (VACV) which were subsequently quantified using the FACSVerse™ (BD Bioscience) instrument equipped with a BD Flow Sensor for quantitative cell counting.

In more detail, 2.5×10⁵ BHK 21 cells (source ATCC® Corp.) were seeded in GMEM/9% FBS/1.8% Ala-Gln into 12 well plates. Cells were infected on the following day with a serial dilution of the MVA virus stock of interest. Following 1 h of incubation at 37 degrees rifampin (100 µg/mL in GMEM/9% FBS/1.8% Ala-Gln) was added. Cells were harvested 19±2 h after infection and fixed and permeabilized with the BDR Co. Perm/Wash™ kit prior to antibody staining. Fixed cells were incubated with anti-vaccinia FITC (Fitzgerald Industries International, Cat #60-v68) for 60-90 minutes. Then, the percentage of virus-positive cells was determined by flow cytometry using the BD® Co. FACS-Verse™ cytometer. The total cell count was determined by using the BD® Co. FACSVerse™ Flow Sensor on unstained cells that were fixed in parallel. The calculation of the virus titer (InfU/mL) was based on the percentage of virus-positive cells, the virus dilution used during infection, the infection volume and the average cell number per well. To limit the effect of well to well variability of the cell count, the cell number was established by averaging the cell count of multiple wells. For calculation of the InfU/mL of the virus sample, only dilutions containing 2 to 35% VACV-positive cells were included. The calculation of the InfU/mL per sample dilution was done according to the following formulas:

$$Inf.\ U/ml =$$
$$average\ cell\ number * \left[ -LN\left(1 - \frac{\%\ VACV\ pos.\ cells}{100}\right)\right] * \frac{virus\ dilution}{infection\ volume}$$

Example 4: Effect of rHSA, Gelatin and Arginine on the Virus Titer at +25 Degrees Celsius Based on results obtained from the FACS assay (see Example 4 above), a virus titer slope was calculated by linear regression analysis for each formulation (see Table 2 below). In general, a higher value of slope is indicative of an increased stability of MVA-BN-RSV within a given formulation.

TABLE 2

| Formulation | Virus titer slope | Std. error | rHSA (%)* | Gelatin (%)* | Arginine (mM) |
|---|---|---|---|---|---|
| F23 | −0.00561 | 0.00137 | 1 | 3 | 0 |
| F70 | −0.00624 | 0.00063 | 0.5 | 3 | 100 |
| F80 | −0.00664 | 0.00072 | 1 | 1.5 | 0 |
| F77 | −0.00684 | 0.00104 | 0.5 | 3 | 0 |
| F69 | −0.00761 | 0.00062 | 0.25 | 3 | 0 |
| F76 | −0.00796 | 0.00081 | 0.5 | 1.5 | 0 |
| F83 | −0.00822 | 0.00109 | 0.5 | 0 | 100 |
| F78 | −0.00828 | 0.00095 | 1 | 0 | 100 |
| F72 | −0.00829 | 0.00056 | 0 | 0 | 100 |
| F74 | −0.0086 | 0.00187 | 0.25 | 0 | 100 |
| F75 | −0.00879 | 0.00165 | 0.25 | 1.5 | 0 |
| F82 | −0.00911 | 0.00106 | 1 | 0 | 0 |
| F85 | −0.00966 | 0.00138 | 0.1 | 3 | 0 |
| F87 | −0.0099 | 0.00107 | 0.1 | 1.5 | 0 |
| F73 | −0.01035 | 0.00184 | 0.5 | 0 | 0 |
| F81 | −0.01106 | 0.00130 | 0 | 1.5 | 0 |
| F88 | −0.01225 | 0.00254 | 0.1 | 0 | 100 |
| F84 | −0.01925 | 0.00241 | 0.25 | 0 | 0 |
| F71 | −0.02584 | 0.00281 | 0.1 | 0 | 0 |
| F86 | −0.02732 | 0.00225 | 0 | 0 | 0 |

TABLE 2-continued

| Formulation | Virus titer slope | Std. error | rHSA (%)* | Gelatin (%)* | Arginine (mM) |
|---|---|---|---|---|---|

*% = w/v

The data of virus titer slope and the respective standard errors shown in Table 2 were processed in FIGS. 2 to 5. The data used in FIG. 1 were obtained in a separate experiment.

FIG. 1 shows that formulation F23 containing 1% rHSA plus 3% gelatin resulted in a significantly flatter slope than formulation (F1) containing 10 mM Tris/140 mM NaCl.

Figure 2:
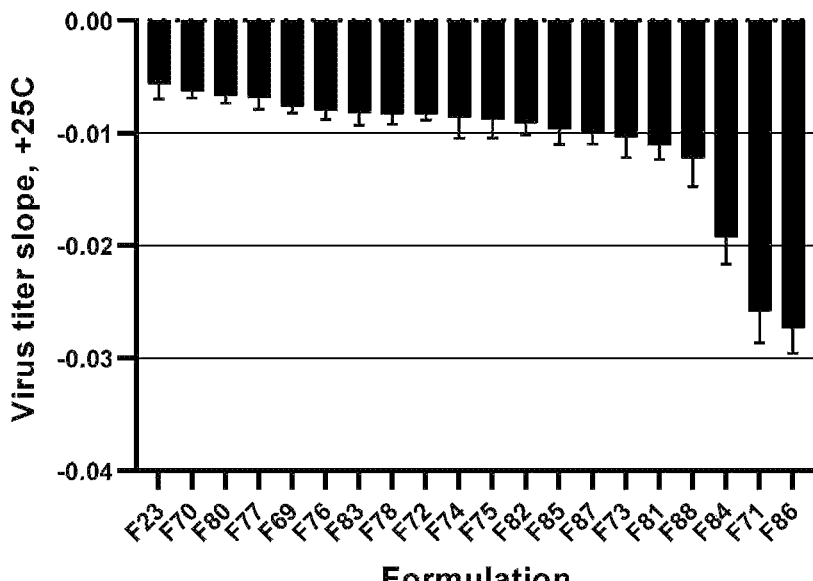
FIG. 2 shows ranked virus titer slopes for different formulations (the compositions of which are specified in Table 1).

In FIG. 2, F23 represents a reference. As depicted, several formulations showed similar values of the virus titer slope as F23. Significantly, there is no difference at least between formulations F23 and F72, and the differences between F23 and F74 to F81 are very low. In contrast, the formulation without rHSA (F86) or formulations containing rHSA at concentrations of 0.1% (F71) and 0.25% (F84), respectively, were not capable of sufficiently maintaining the stability of MVA-BN-RSV.

Figure 3:
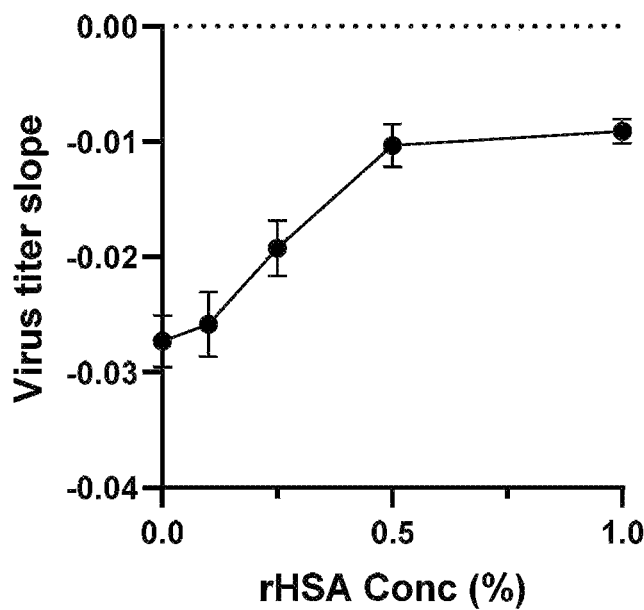
FIG. 3 shows the effect of rHSA on the virus titer slope. The formulations contained 0-1.0% (w/v) rHSA in 10 mM Tris/140 mM NaCl, 10% (w/v) sucrose, 2% (w/v) sorbitol (base buffer).

FIG. 3 illustrates data obtained from formulations containing only rHSA in the base composition (10 mM Tris/140 mM NaCl containing 10% sucrose and 2% sorbitol. As demonstrated, the stability of MVA-BN-RSV increased from 0.1% to 0.5% rHSA. No significant difference in the slope of the virus titer was observed between 0.5% and 1.0% rHSA. Particularly, no further increase in stability occurred between 0.5% and 1% rHSA. Thus, a concentration of 0.5% rHSA is enough for producing an acceptable virus stability.

Figure 4:
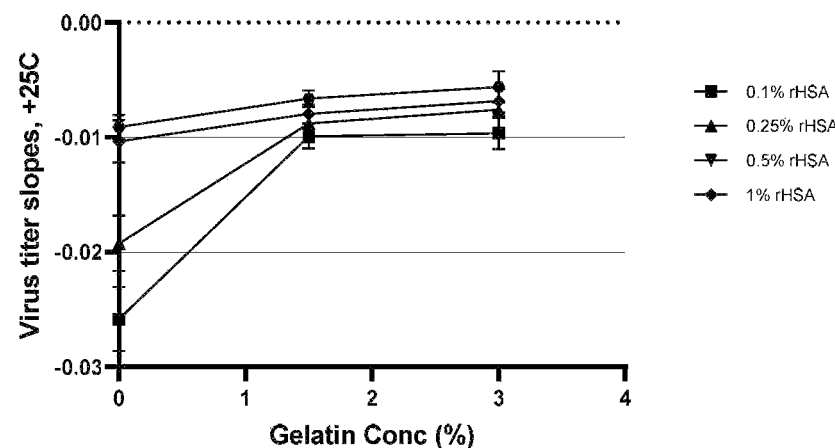
FIG. 4 shows the effect of gelatin on the virus titer slope. The formulations contained 0-3.0% (w/v) gelatin in base buffer and rHSA at the indicated concentrations.

FIG. 4 shows that different concentrations of rHSA produced similar values of the virus titer slope if gelatin was present at concentrations of 1.5% to 3%. Accordingly, 1.5% to 3% gelatin is capable of compensating for reduced rHSA concentrations. Acceptable stability was obtained already with a formulation containing 1.5% gelatin plus 0.1% rHSA being comparable to formulation F23 containing 3% gelatin and 1% rHSA.

Figure 5:
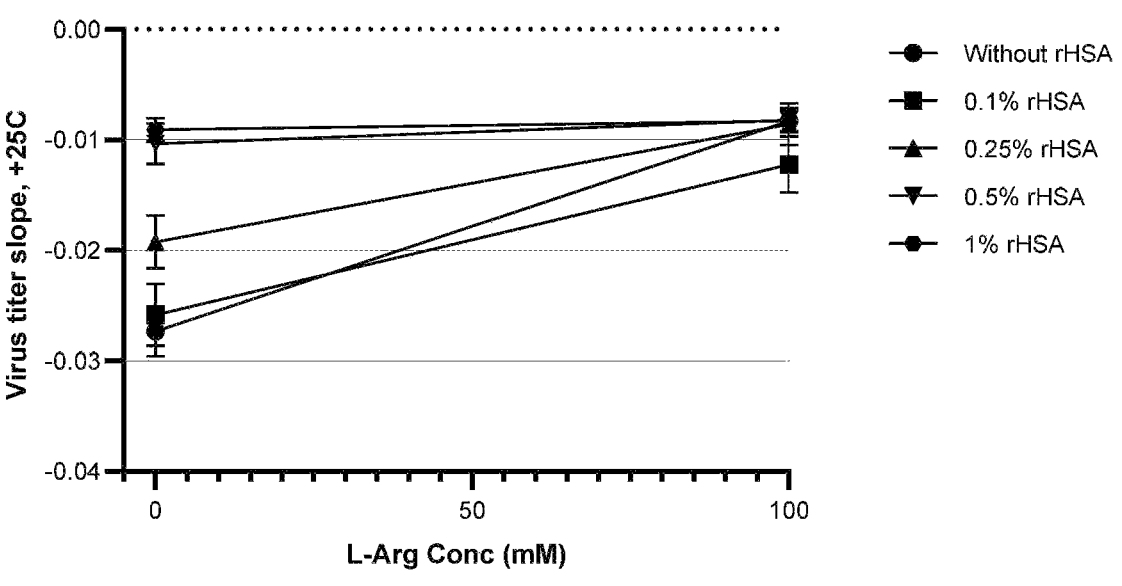
FIG. 5 shows the effect of arginine on the virus titer slope. The formulations contained no (0 mM) or 100 mM arginine in base buffer and rHSA at the indicated concentrations.

As discussed in the context of FIG. 3 (see above), the stabilizing capability of rHSA depended on its concentration. FIG. 5 shows that the additional presence of 100 mM arginine produced similar virus titer slopes for all rHSA concentrations tested. Notably, no significant effect of arginine was observed in the formulations containing 0.5% or 1% rHSA. All in all, the results shown in FIG. 5 indicate that 100 mM arginine alone is capable of producing similar virus titer slopes as found with high concentrations of rHSA.

In summary, rHSA, gelatin and arginine have the potential to improve the stability of MVA-BN-RSV.

Particularly, formulation F23 containing 1% rHSA plus 3% gelatin is known to stabilize MVA-BN-RSV very well (FIGS. 1 and 2). Formulations containing 0.5% rHSA (F73) and 0.1% rHSA plus 1.5% gelatin (F87), respectively, show slightly lesser stabilization capabilities which, however, are still in a similar order as seen with F23 (FIG. 2). Advantageously, F73 and F87 contain lower concentration of rHSA and gelatin as compared to F23.

Similarly, the formulation containing 100 mM arginine instead of rHSA and gelatin (F72) seems to stabilize MVA-BN-RSV slightly lesser than F23 (FIG. 2). Advantageously, however, F72 is free of expensive rHSA as wells as gelatin.

Example 5: Effect of HSA, Gelatin and Arginine on the pH

As an indirect parameter of stability, the pH of the formulations was determined. An increase in pH may point to an instability.

Based on these results, a pH slope for each formulation was calculated using linear regression analysis (see Table 3 below).

TABLE 3

| Formulation | pH slope | Std. error | rHSA (%)* | Gelatin (%)* | Arginine (mM) |
|---|---|---|---|---|---|
| F70 | −0.00150 | 0.00017 | 0.5 | 3 | 100 |
| F23 | −0.00209 | 0.00097 | 1.0 | 3 | 0 |
| F69 | −0.00210 | 0.00048 | 0.25 | 3 | 0 |
| F85 | −0.00235 | 0.00017 | 0.1 | 3 | 0 |
| F77 | −0.00259 | 0.00019 | 0.5 | 3 | 0 |
| F72 | −0.00308 | 0.00157 | 0 | 0 | 100 |
| F76 | −0.00309 | 0.00004 | 0.5 | 1.5 | 0 |
| F81 | −0.00387 | 0.00061 | 0 | 1.5 | 0 |
| F75 | −0.00391 | 0.00004 | 0.25 | 1.5 | 0 |
| F80 | −0.00396 | 0.00018 | 1.0 | 1.5 | 0 |
| F74 | −0.00405 | 0.00044 | 0.25 | 0 | 100 |
| F87 | −0.00418 | 0.00002 | 0.1 | 1.5 | 0 |
| F83 | −0.00423 | 0.00051 | 0.5 | 0 | 100 |
| F88 | −0.00493 | 0.00163 | 0.1 | 0 | 100 |
| F78 | −0.00508 | 0.00057 | 1.0 | 0 | 100 |
| F86 | −0.00910 | 0.00115 | 0 | 0 | 0 |
| F82 | −0.00921 | 0.00103 | 1 | 0 | 0 |
| F84 | −0.00953 | 0.00121 | 0.25 | 0 | 0 |
| F71 | −0.01003 | 0.00168 | 0.1 | 0 | 0 |
| F73 | −0.01196 | 0.00301 | 0.5 | 0 | 0 |

*% = w/v

The pH slope data and standard errors shown in Table 3 were processed in FIGS. 7 to 10. The data used in FIG. 6 were obtained in a separate experiment.

Figure 6:
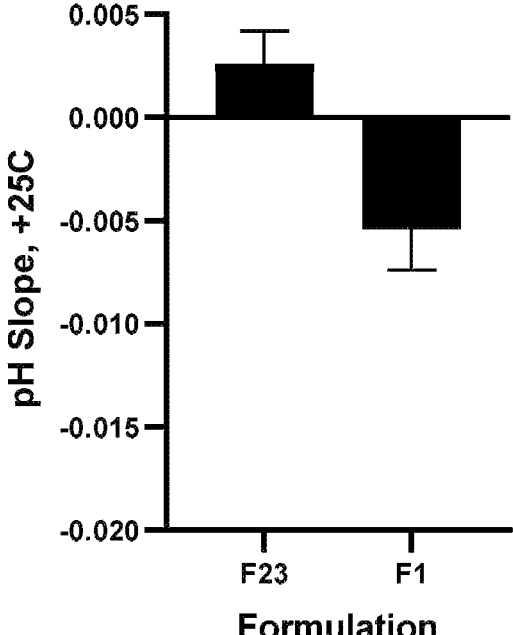
FIG. 6 shows pH slopes (change in pH over time, i.e. change/day) for formulation F1 (10 mM Tris/140 mM NaCl) and formulation F23 (1% (w/v) rHSA, 3% (w/v) gelatin in base buffer). The pH slopes were calculated by means of linear regression analysis of pH values determined at study start (time zero, t=0) and after 3 weeks (19 days) and 5 weeks (33 days) of incubation at +25 degrees Celsius. The error bars indicate the standard errors for each pH slope.

FIG. 6 shows the difference in pH stability between formulation F23 containing 1% rHSA plus 3% gelatin and formulation F1 containing 10 mM Tris/140 mM NaCl.

Figure 7:
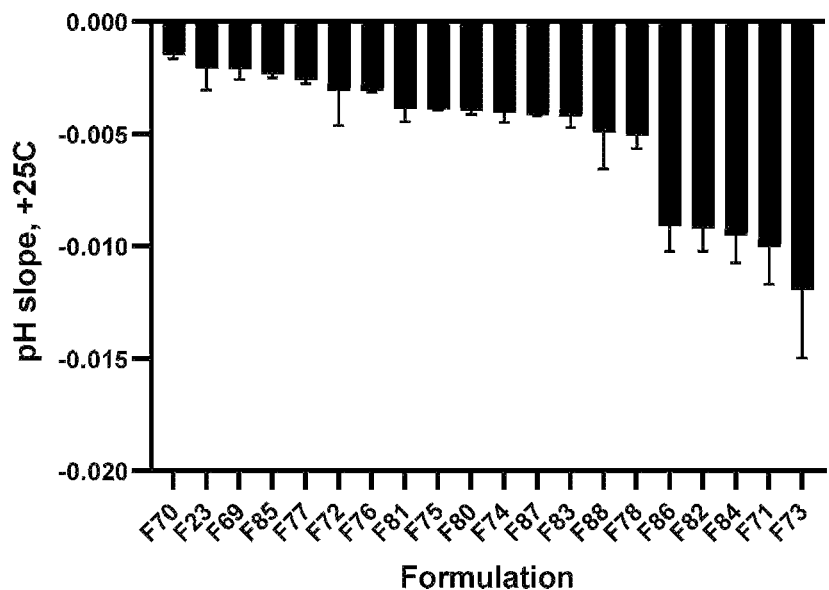
FIG. 7 shows the ranked pH slopes for different formulations (the compositions of which are specified in Table 1).
Figure 8:
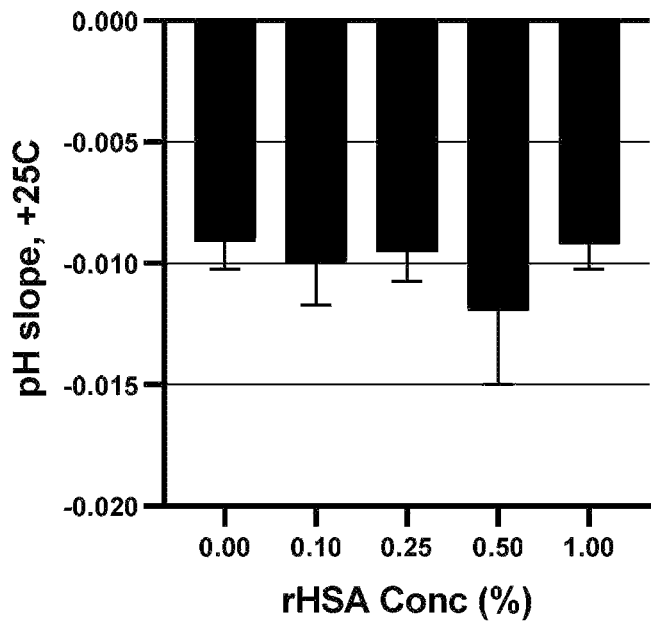
FIG. 8 shows the effect of rHSA on the pH slope. The formulations (F71, F73, F82, F84, and F86) contained 0-1.0% (w/v) rHSA in base buffer.
Figure 9:
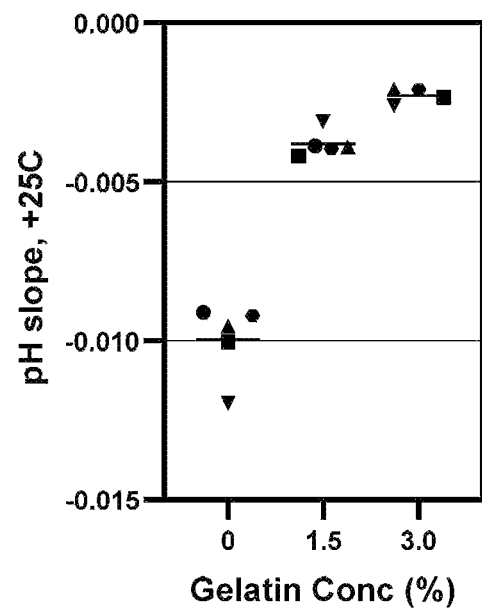
FIG. 9 shows the effect of gelatin on the pH slope. The formulations contained no (0%), 1.5% (w/v) or 3.0% (w/v) gelatin in base buffer and rHSA at different concentrations.
Figure 10:
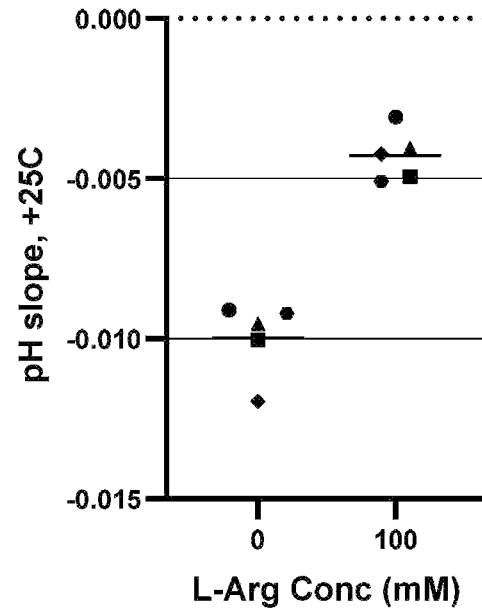
FIG. 10 shows the effect of arginine on the virus titer slope. The formulations contained no (0 mM) or 100 mM arginine in base buffer and rHSA at different concentrations.

As shown in FIGS. 7 and 8, rHSA had no stabilizing effect on the pH of the formulations. In contrast, gelatin at concentrations of 1.5% and 3% increased the pH stability independently of the presence or concentration of rHSA (FIG. 9). Similarly, 100 mM arginine increased the pH stability of the formulations independently of rHSA (FIG. 10).

Example 6: Effect of rHSA, Gelatin and Arginine on the Virus Titer During Freeze-Thaw Cycles In another study, formulations were exposed to freeze-thaw (F/T) cycles (−50 degrees Celsius/ambient temperature)

A liner regression analysis was performed on virus titers obtained at study start (time zero, t=0) and after 5 F/T cycles and 10 F/T cycles (see Table 4 below).

TABLE 4

| Formulation | Virus titer slope | Std. error | rHSA (%)* | Gelatin (%)* | Arginine (mM) |
|---|---|---|---|---|---|
| F75 | 0.00270 | 0.00354 | 0.25 | 1.5 | 0 |
| F72 | 0.00255 | 0.00282 | 0 | 0 | 100 |
| F69 | 0.00055 | 0.00313 | 0.25 | 3 | 0 |
| F70 | −0.00031 | 0.00477 | 0.5 | 3 | 100 |
| F23 | −0.00063 | 0.00279 | 1.0 | 3 | 0 |
| F89 | −0.00435 | 0.00435 | 0.25 | 1.5 | 100 |
| F74 | −0.00449 | 0.00249 | 0.25 | 0 | 100 |
| F86 | −0.01391 | 0.00339 | 0 | 0 | 0 |

*% = w/v; F89: 0.25% rHSA, 1.5% gelatin, 100 mM arginine.

Figure 11:
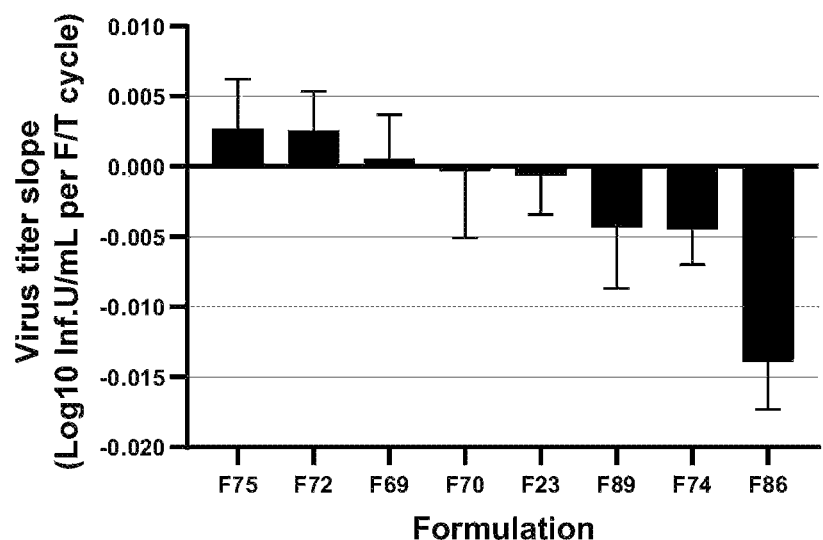
FIG. 11 shows ranked virus titer slopes for formulations exposed to freeze-thaw (F/T) cycles. The virus titer slopes were calculated by means of linear regression analysis of virus titers determined at study start (time zero, t=0) and after 5 F/T cycles and 10 F/T cycles (−50 degrees Celsius/ambient temperature).

The data of the virus titer slope and the respective standard errors shown in Table 4 were processed in FIG. 11.

FIG. 11 shows that formulations F75 (0.25% rHSA, 1.5% gelatin) and F72 (100 mM arginine) have good virus stabilities after F/T cycles. Additionally, the pH is not affected by F/T cycles (data not shown).

REFERENCES

Al Yaghchi, C., Zhang, Z., Alusi, G., Lemoine, N. R., and Wang, Y. (2015). Vaccinia virus, a promising new therapeutic agent for pancreatic cancer. Immunotherapy 7: 1249-1258.

Baur, K., Brinkmann, K., Schweneker, M., Patzold, J., Meisinger-Henschel, C., Hermann, J., Steigerwald, R., Chaplin, P., Suter, M., and Hausmann, J. (2010). Immediate-early expression of a recombinant antigen by modified vaccinia virus ankara breaks the immunodominance of strong vector-specific B8R antigen in acute and memory CD8 T-cell responses. J Virol 84: 8743-8752.

Berhanu, A., King, D. S., Mosier, S., Jordan, R., Jones, K. F., Hruby, D. E., and Grosenbach, D. W. (2010). Impact of ST-246(R) on ACAM2000 smallpox vaccine reactogenicity, immunogenicity, and protective efficacy in immunodeficient mice. Vaccine 29: 289-303.

Burke, C. J., Hsu, T. A., and Volkin, D. B. (1999). Formulation, stability, and delivery of live attenuated vaccines for human use. Crit Rev Ther Drug Carrier Syst 16: 1-83.

Capelle, M. A. H., Babich, L., van Deventer-Troost, J. P. E., Salerno, D., Krijgsman, K., Dirmeier, U., Raaby, B., and Adriaansen, J. (2018). Stability and suitability for storage and distribution of Ad26.ZEBOV/MVA-BN(R)-Filo heterologous prime-boost Ebola vaccine. Eur J Pharm Biopharm 129: 215-221.

Chakrabarti, S., Sisler, J. R., and Moss, B. (1997). Compact, synthetic, vaccinia virus early/late promoter for protein expression. Biotechniques 23: 1094-1097.

Choi, Y., and Chang, J. (2013). Viral vectors for vaccine applications. Clin Exp Vaccine Cochran, M. A., Puckett, C., and Moss, B. (1985). In vitro mutagenesis of the promoter region for a vaccinia virus gene: evidence for tandem early and late regulatory signals. J Virol 54: 30-37.

Filipe, V., Hawe, A., and Jiskoot, W. (2010). Critical evaluation of Nanoparticle Tracking Analysis (NTA) by NanoSight for the measurement of nanoparticles and protein aggregates. Pharm Res 27: 796-810.

Hekker, A. C., J. M., B., and Smith, L. (1973). A stable freeze-dried smallpox vaccine made in monolayer cultures of primary rabbit kidney cells. Journal of Biological Standardization 1: 21-32.

Hodge, J. W., Sabzevari, H., Yafal, A. G., Gritz, L., Lorenz, M. G., and Schlom, J. (1999). A triad of costimulatory molecules synergize to amplify T-cell activation. Cancer Res 59: 5800-5807.

Just, I., and Finke, H. (1979). [A contribution to the stabilisation of the MVA-vaccine (author's transl)]. Zentralbl Bakteriol Orig A 245: 276-282.

Leon, A., David, A. L., Madeline, B., Guianvarc'h, L., Dureau, E., Champion-Arnaud, P., Hebben, M., Huss, T., Chatrenet, B., and Schwamborn, K. (2016). The EB66(R) cell line as a valuable cell substrate for MVA-based vaccines production. Vaccine 34: 5878-5885.

Mastrangelo, M. J., Eisenlohr, L. C., Gomella, L., and Lattime, E. C. (2000). Poxvirus vectors: orphaned and underappreciated. J Clin Invest 105: 1031-1034.

Mayr, A., and Danner, K. (1978). Vaccination against pox diseases under immunosuppressive conditions. Dev Biol Stand 41: 225-234.

Mayr, A., Hochstein-Mintzel, V., and Stickl, H. (1975). Abstammung, Eigenschaften and Verwendung des attenuierten Vaccinia-Stammes MVA. *Infektion* 3: 6-14

Meyer, H., Sutter, G., and Mayr, A. (1991). Mapping of deletions in the genome of the highly attenuated vaccinia virus MVA and their influence on virulence. *J Gen Virol* 72 (Pt 5): 1031-1038.

Otagiri, M., and Chuang, V. T. (2009). Pharmaceutically important pre- and posttranslational modifications on human serum albumin. *Biol Pharm Bull* 32: 527-534.

Prabhu, M., Bhanuprakash, V., Venkatesan, G., Yogisharadhya, R., Bora, D. P., and Balamurugan, V. (2014). Evaluation of stability of live attenuated camelpox vaccine stabilized with different stabilizers and reconstituted with various diluents. *Biologicals* 42: 169-175.

Rezaee, F., Linfield, D. T., Harford, T. J., and Piedimonte, G. (2017). Ongoing developments in RSV prophylaxis: a clinician's analysis. *Curr Opin Virol* 24: 70-78.

Schweneker, M., Laimbacher, A. S., Zimmer, G., Wagner, S., Schraner, E. M., Wolferstatter, M., Klingenberg, M., Dirmeier, U., Steigerwald, R., Lauterbach, H., et al. (2017). Recombinant Modified Vaccinia Virus Ankara Generating Ebola Virus-Like Particles. *J Virol* 91: e00343-00317.

Suter, M., Meisinger-Henschel, C., Tzatzaris, M., Hulsemann, V., Lukassen, S., Wulff, N. H., Hausmann, J., Howley, P., and Chaplin, P. (2009). Modified vaccinia Ankara strains with identical coding sequences actually represent complex mixtures of viruses that determine the biological properties of each strain. *Vaccine* 27: 7442-7450.

Tlaxca, J. L., Ellis, S., and Remmele, R. L., Jr. (2015). Live attenuated and inactivated viral vaccine formulation and nasal delivery: potential and challenges. *Adv Drug Deliv Rev* 93: 56-78.

Vanderplasschen, A., and Pastoret, P. P. (2003). The uses of poxviruses as vectors. *Curr Gene Ther* 3: 583-595.

Verheust, C., Goossens, M., Pauwels, K., and Breyer, D. (2012). Biosafety aspects of modified vaccinia virus Ankara (MVA)-based vectors used for gene therapy or vaccination. *Vaccine* 30: 2623-2632.

Wennier, S. T., Brinkmann, K., Steinhausser, C., Maylander, N., Mnich, C., Wielert, U., Dirmeier, U., Hausmann, J., Chaplin, P., and Steigerwald, R. (2013). A novel naturally occurring tandem promoter in modified vaccinia virus ankara drives very early gene expression and potent immune responses. *PLoS One* 8: e73511.

Zhang, Y.-z., Jiang, C.-l., Yu, X.-h., Lou, C.-p., Zhao, D.-h., Wu, Y.-g., Jin, Y.-h., Liu, C.-s., and Kong, W. (2007). Immunogenicity of Lyophilized MVA Vaccine for HIV-1 in Mice Model. *Chemical Research in Chinese Universities* 23: 329-332.

Maity H, O'Dell C, Srivastava A, Goldstein J. Effects of arginine on photostability and thermal stability of IgG1 monoclonal antibodies. *Curr Pharm Biotechnol* 2009; 10:761-6

Maity H, karkaraia C, Davagnino J. Effects of pH and arginine on the solubility and stability of a therapeutic protein (Fibroblast Growth Factor 20): relationship between solubility and stability. *Curr Pharm Biotechnol* 2009; 10:609-25

Mistilis M J, Bommarius A S, Prausnitz M R. Development of a thermostable microneedle patch for influenza vaccination. *J Pharm Sci* 2015; 104:740-9

Cardoso, F. M. C., Petrovajova, D., and Hornakova, T. (2017). Viral vaccine stabilizers: status and trends. *Acta virologica* 61: 231-239

Evans R K, Nowrocki D K, Isopi L A, Williams D M, Casimiro D R, Chin S, Chen M, Zhu D M, Shiver J W, Volkin D B. Development of stable liquid formulations for adenovirus-based vaccines. *J Pharm Sci*. 2004 October; 93(10):2458-75

White J A, Estrada M, Flood E A, Mahmood K, Dhere R, Chen D. Development of a stable liquid formulation of live attenuated influenza vaccine. *Vaccine* 34 (2016) 3676-3683

We claim:

1. An aqueous composition consisting of:
   arginine;
   Tris buffer;
   sodium chloride;
   sucrose;
   sorbitol; and
   a poxvirus.

2. The composition according to claim 1 that comprises said arginine at a concentration of from 50 mM to 150 mM, 75 mM to 125 mM, 80 mM to 120 mM, 90 mM to 110 mM, 95 mM to 105 mM, or 100 mM.

3. The composition according to claim 1 that comprises said Tris buffer at a concentration of 10 mM.

4. The composition according to claim 1 that comprises said sodium chloride at a concentration of 140 mM.

5. The composition according to claim 1 that comprises said sucrose at a concentration of 10% (w/v).

6. The composition according to claim 1 that comprises said sorbitol at a concentration of 2% (w/v).

7. The composition according to claim 1, wherein said poxvirus is MVA.

8. The composition according to claim 1 that has a pH of from pH 7.0 to pH 8.5.

9. The composition according to claim 2 wherein said poxvirus is MVA.

10. The composition according to claim 1 that comprises: 50 mM to 150 mM arginine; 10 mM Tris buffer; 140 mM sodium chloride; 10% (w/v) sucrose; and 2% (w/v) sorbitol.

11. The composition according to claim 10 that comprises poxvirus at a titer of between about $1 \times 10^7$ to $6 \times 10^9$ InfU/mL.

12. The composition according to claim 11 that comprises MVA-BN or recombinant MVA-BN.

13. The composition according to claim 12 that comprises a recombinant MVA-BN that encodes at least one respiratory syncytial virus (RSV) protein or a part thereof.

14. A vaccine comprising the composition of claim 12.

15. A method of preparing a composition for storing a poxvirus, comprising the steps of:
   (i) providing a preparation comprising a poxvirus in a pharmaceutically acceptable buffer; and
   (ii) combining the poxvirus preparation of step (i) with an aqueous composition consisting of arginine, Tris buffer, sodium chloride, sucrose, and sorbitol to provide a composition of any one of claims 1-12.

16. The method of claim 15, wherein the poxvirus is a recombinant MVA encoding at least one respiratory syncytial virus (RSV) protein or a part thereof.

17. The method of claim 15, wherein the composition for storing the poxvirus is stable for at least 2 years at −50 degrees Celsius or −20 degrees Celsius.

18. The method of claim 15, wherein the composition for storing the poxvirus is stable for at least 6 months at +5 degrees Celsius, +20 degrees Celsius or +25 degrees Celsius.

19. A method of preparing a composition according to claim 12, the method comprising the steps of:

(i) providing a preparation comprising a poxvirus that is MVA-BN or recombinant MVA-BN in a pharmaceutically acceptable buffer, and (ii) combining the poxvirus preparation of step (i) with an aqueous composition consisting of arginine, Tris buffer, sodium chloride, sucrose, and sorbitol to provide the composition according to any one of claims 1 to 11.

20. The method according to claim 19, wherein the poxvirus is recombinant MVA encoding at least one respiratory syncytial virus (RSV) protein or a part thereof.

21. An aqueous composition having a pH of from pH 7.0 to pH 8.5 consisting of: poxvirus, arginine at a concentration of from 50 mM to 150 mM, Tris buffer, sodium chloride, sucrose, and sorbitol; and free of a chelating agent and/or glutamic acid.

* * * * *